United States Patent
Traxler et al.

Patent Number: 6,140,317
Date of Patent: Oct. 31, 2000

[54] PYRROLOPYRIMIDINES AND PROCESSES FOR THEIR PREPARATION

[75] Inventors: Peter Traxler, Schönenbuch; Jörg Frei, Hölstein; Guido Bold, Gipf-Oberfrick, all of Switzerland

[73] Assignee: Novartis AG, Basel, Switzerland

[21] Appl. No.: 09/117,056

[22] PCT Filed: Jan. 13, 1997

[86] PCT No.: PCT/EP97/00127

§ 371 Date: Jul. 22, 1998

§ 102(e) Date: Jul. 22, 1998

[87] PCT Pub. No.: WO97/27199

PCT Pub. Date: Jul. 31, 1997

[30] Foreign Application Priority Data

Jan. 23, 1996 [CH] Switzerland ............... 175/96

[51] Int. Cl.$^7$ .......... A01N 43/00; A61K 31/50; C07D 491/00; C07D 239/00; C07F 5/02
[52] U.S. Cl. .......... 514/183; 514/213; 514/253; 514/258; 514/267; 540/476; 540/593; 544/229; 544/250; 544/280
[58] Field of Search ............ 540/476, 593; 544/280, 250, 229; 514/183, 213, 253, 258, 267

[56] References Cited

U.S. PATENT DOCUMENTS

| | | | |
|---|---|---|---|
| 5,686,457 | 11/1997 | Traxler et al. | 514/258 |
| 5,736,534 | 4/1998 | Arnold | 514/63 |

FOREIGN PATENT DOCUMENTS

| | | |
|---|---|---|
| 514 540 A1 | 11/1992 | European Pat. Off. . |
| WO 94/17803 | 8/1994 | WIPO . |
| WO 95/19774 | 7/1995 | WIPO . |
| WO 95/23141 | 8/1995 | WIPO . |
| WO 96/31510 | 10/1996 | WIPO . |
| 96/40142 | 12/1996 | WIPO . |
| WO 97/02266 | 1/1997 | WIPO . |
| 98/23613 | 6/1998 | WIPO . |

OTHER PUBLICATIONS

Burke, "Protein–Tyrosine Kinases: Potential Targets for Anticancer Drug Development," STEM CELLS, vol. 12, pp. 1–6, 1994.

Thompson et al., J. Med. Chem., vol. 38, pp. 3780–88 (1995).
Spada et al., Exp.Opin.Ther.Patents, vol. 5 (8) pp. 805–817 (1995).
Ramsay et al., Synthetic Communications, vol. 25(24), pp. 4029–4033 (1995).
Gribble et al., Synthesis, pp. 859–860 (1977).

*Primary Examiner*—Mukund J. Shah
*Assistant Examiner*—Tamthom N. Truong
*Attorney, Agent, or Firm*—Joseph J. Borovian

[57] ABSTRACT

There are described compounds of formula I

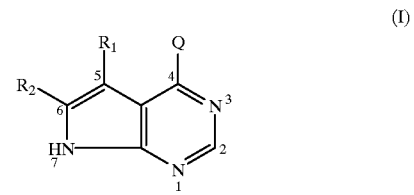

wherein $R_1$ and $R_2$ are as defined in the description, Q is heterocyclyl boned via a ring nitrogen atom and having the formula IA

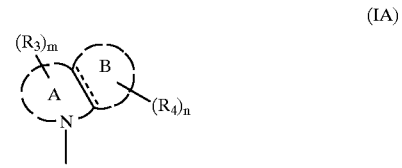

wherein $R_3$ and $R_4$ and m and n are as defined in the description, the ring marked A is a heterocyclyl having 5 to 9 ring atoms and having at least one saturated bond, it being possible for a further ring hetero atom selected from O and S to be present in addition to the bonding nitrogen atom, the ring system marked B is a free or benzo-, thieno-, furo-, pyrrolo- or dihydropyrrolo-fused carbocyclic ring having from 5 to 9 carbon atoms that is fused to the ring A and may be unsaturated, partially saturated or fully saturated, and the bond marked by a parallel dotted line between the ring systems marked A and B is either a single bond or a double bond, and a salt thereof where at least one salt-forming group is present. The compounds are inhibitors of protein kinases and have, for example, antitumour activity.

13 Claims, No Drawings

PYRROLOPYRIMIDINES AND PROCESSES FOR THEIR PREPARATION

This is a 371 application of PCT/EP 97/00127 filed Jan. 13, 1997.

The invention relates to 7H-pyrrolo[2,3-d]pyrimidine derivatives and to processes and novel intermediates for their preparation, to pharmaceutical formulations comprising such derivatives, and to the use of those derivatives as medicaments, and to their use in the preparation of medicaments.

The compounds according to the invention are compounds of formula I

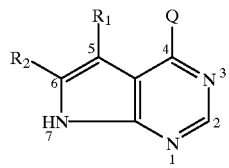

(I)

wherein $R_1$ and $R_2$ are each independently of the other lower alkyl; monohalo-, dihalo- or trihalo-lower alkyl; lower alkoxy; phenyl that is unsubstituted or substituted by halogen, monohalo-, dihalo- or trihalo-lower alkyl, carbamoyl-methoxy, carboxy-methoxy, benzyloxycarbonyl-methoxy, lower alkoxycarbonyl-methoxy, phenyl, amino, amino-lower alkyl, lower alkanoylamino, lower alkoxycarbonylamino, phenyl-lower alkoxycarbonylamino, furoyl, thienylcarbonyl, N-lower alkylamino, N,N-di-lower alkyl-amino, hydroxy, lower alkoxy, lower alkanoyloxy, carboxy, lower alkoxycarbonyl, carbamoyl, N-lower alkyl-carbamoyl, N,N-di-lower alkyl-carbamoyl, cyano, amidino, N-(N',N'-di-lower alkylaminomethylidene)-amino, N-((N',N'-di-lower alkylamino)-(lower alkyl)-methylidene)-amino, guanidino, ureido, $N^3$-lower alkylureido, $N^3,N^3$-di-lower alkylureido, thioureido, $N^3$-lower alkylthioureido, $N^3,N^3$-di-lower alkylthioureido, lower alkanesulfonylamino, benzene- or naphthalene-sulfonylamino that is unsubstituted or lower alkyl-substituted at the benzene or naphthalene ring, azido or by nitro; hydrogen; unsubstituted or halo- or lower alkyl-substituted pyridyl; N-benzyl-pyridonium; naphthyl; cyano; carboxy; lower alkoxycarbonyl; carbamoyl; N-lower alkyl-carbamoyl; N,N-di-lower alkyl-carbamoyl; N-benzyl-carbamoyl; formyl; lower alkanoyl; lower alkenyl; lower alkenyioxy; or lower alkyl substituted by halogen, amino, lower alkyiamino, piperazino, di-lower alkylamino, phenylamino or phenyl (each unsubstituted or substituted in the phenyl moiety by halogen, lower alkyl, hydroxy, lower alkanoyloxy, lower alkoxy, carboxy, lower alkoxycarbonyl, carbamoyl, N-lower alkyl-carbamoyl, N,N-di-lower alkyl-carbamoyl, cyano, amidino, amino, amino-lower alkyl, lower alkanoylamino, lower alkylamino, N,N-di-lower alkylamino or by trifluoromethyl), hydroxy, lower alkoxy, cyano, carboxy, lower alkoxycarbonyl, carbamoyl, N-lower alkyl-carbamoyl, N,N-di-lower alkyl-carbamoyl, mercapto or by a radical of the formula $R_5$—$S(O_q)$— wherein $R_5$ is lower alkyl and q is 0, 1 or 2, or $R_1$ and $R_2$ together form an alkylene chain having from 2 to 5 carbon atoms which is unsubstituted or substituted by lower alkyl, Q is heterocyclyl bonded via a ring nitrogen atom and having the formula IA

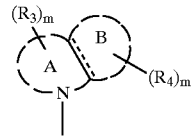

(IA)

wherein m and n are each independently of the other from 0 to 3, $R_3$ and $R_4$ are each independently of the other selected from lower alkyl; amino-lower alkyl; N-lower alkyl-amino-lower alkyl; N,N-di-lower alkylamino-lower alkyl; lower alkenyl; lower alkynyl; tri-lower alkylsilanyl-lower alkynyl; monohalo-, dihalo- or trihalo-lower alkyl; halogen; nitro; hydroxy; lower alkoxy; lower alkanoyloxy; isothiocyanato; phenyl that is unsubstituted or substituted by halogen, nitro, trihalo-lower alkyl, hydroxy or by lower alkyl; thienyl; phenyl-lower alkoxy that is unsubstituted or substituted in the phenyl ring by halogen, nitro, trihalo-lower alkyl, hydroxy or by lower alkyl; carboxy; lower alkoxycarbonyl; carbamoyl; N-lower alkylcarbamoyl; N,N-di-lower alkylcarbamoyl; cyano; amino; N-lower alkylamino; N,N-di-lower alkylamino; azido; benzoylamino that is unsubstituted or substituted in the benzene ring by halogen, nitro, tri-halo-lower alkyl, hydroxy or by lower alkyl; lower alkanoylamino; monohalo-, dihalo- or trihalo-lower alkylcarbonylamino; lower alkanesulfonylamino; trihalo-lower alkanesulfonylamino; lower alkylthio; lower alkylsulfinyl; lower alkanesulfonyl; pyrrol-1-yl; piperidin-1-yl; pyrrolidin-1-yl and lower alkanoyl, or two radicals $R_3$ together or two radicals $R_4$ together form lower alkylenedioxy;

the ring marked A is a heterocyclyl having from 5 to 9 ring atoms and having at least one saturated bond, it being possible for a further ring hetero atom selected from O and S to be present in addition to the bonding nitrogen atom;

the ring system marked B is a free or benzo-, thieno-, furo-, pyrrolo- or dihydropyrrolo-fused carbocyclic ring having from 5 to 9 carbon atoms that is fused to the ring A and may be unsaturated, partially saturated or fully saturated; and the bond marked by a parallel dotted line between the ring systems marked A and B is either a single bond or a double bond;

and salts thereof where at least one salt-forming group is present.

The term "lower" used hereinabove and hereinbelow denotes a radical having up to and including a maximum of 7, especially up to and including a maximum of 4, carbon atoms, and especially (unless indicated to the contrary) having 1 or 2 carbon atoms.

Where the compounds of formula I contain asymmetric centers, they may be in the form of mixtures of enantiomers, and where several asymmetric centers are present also in the form of diastereoisomeric mixtures; when double bonds are present, cis/trans isomers are possible. The compounds of formula I are preferably in the form of pure isomers.

Carbon atoms the substituents of which are not otherwise defined are bonded to hydrogen atoms; where the number of substituents is variable, a carbon atom will have as many substituents and hydrogen atoms as will result in the carbon atom in question being neutral and having a complete electron octet.

Lower alkyl is preferably n-butyl, n-propyl, isopropyl, ethyl or especially methyl.

Halogen is bromine, iodine or preferably fluorine or especially chlorine.

Monohalo-, dihalo- or trihalo-lower alkyl is especially trifluoromethyl.

Lower alkoxy is especially methoxy.

Monohalo-, dihalo- or trihalo-lower alkyl is especially monofluoro-, difluoro- or (especially) trifluoro-methyl.

Lower alkoxycarbonyl-methoxy is especially methoxycarbonyl-methoxy.

Amino-lower alkyl is especially aminomethyl.

Phenyl-substituted phenyl $R_1$ or $R_2$ is, for example, biphenylyl, especially 4-biphenylyl.

Lower alkanoylamino is especially acetylamino, propionylamino, n-butyrylamino or isobutyrylamino.

Lower alkoxycarbonylamino is especially methoxycarbonylamino or more especially tert-butoxycarbonylamino.

Phenyl-lower alkoxycarbonylamino is preferably benzyloxycarbonylamino.

Furoyl is especially furan-2-carbonyl.

Thienylcarbonyl is especially thienyl-2-carbonyl.

Lower alkylamino is, for example, propylamino, ethylamino or especially methylamino.

N,N-Di-lower alkylamino is especially dimethylamino.

Lower alkanoyloxy is especially acetoxy.

Lower alkoxycarbonyl is especially tert-butoxycarbonyl or more especially methoxycarbonyl.

N-Lower alkyl-carbamoyl is, for example, N-methylcarbamoyl, N-(n-butyl)-carbamoyl or N-(2-methyl-but-1-yl)-carbamoyl.

N,N-Di-lower alkyl-carbamoyl is, for example, N,N-dimethyl-carbamoyl.

N-(N',N'-Di-lower alkylamino-methylidene)-amino is especially N-(N',N'-dimethylamino-methylidene)-amino.

N-((N',N'-Di-lower alkylamino)-(lower alkyl) methylidene)-amino is especially N-((N',N'-di-methylamino)-(isopropylamino)methylidene)-amino.

$N^3$-Lower alkylureido is especially $N^3$-methylureido ($CH_3$—NH—(C=O)—NH—).

$N^3,N^3$-Di-lower alkylureido is especially $N^3,N^3$-dimethylureido ([$(CH_3)_2$—N—(C=O)—NH—).

$N^3$-Lower alkylthioureido is especially $N^3$-methylthioureido ($CH_3$—NH—(C=S)—NH—).

$N^3,N^3$-Di-lower alkylthioureido is especially $N^3,N^3$-dimethylthioureido ([$(CH_3)_2$—N—(C=S)—NH—).

Lower alkanesulfonylamino is especially N-methanesulfonylamino ($CH_3$—(S{=O}$_2$)—NH—).

Benzene- or naphthalene-sulfonylamino that is unsubstituted or lower alkyl-substituted at the benzene or naphthalene ring is especially 4-toluenesulfonylamino or benzenesulfonyl-amino.

Substituted phenyl $R_1$ or $R_2$ may carry one or more substituents, but preferably not more than 3 substituents, which may be identical or different from one another. Preferably, substituted phenyl $R_1$ or $R_2$ carries only one substituent in the ortho-position or, preferably, in the meta- or para-position. Substituted phenyl $R_1$ or $R_2$ is preferred to unsubstituted phenyl.

Unsubstituted or halo- or lower alkyl-substituted pyridyl is especially 2-pyridyl.

N-Benzyl-pyridonium is especially N-benzyl-pyridonium-2-yl.

Naphthyl is, for example, 2-naphthyl.

Lower alkanoyl is, for example, isobutyryl, butyryl, propionyl or especially acetyl.

Amino-lower alkyl is especially 3-aminopropyl.

N-Lower alkyl-amino-lower alkyl is especially 3-(N-methylamino)-propyl.

N,N-Di-lower alkylamino-lower alkyl is especially 3-(N,N-dimethylamino)-propyl.

Lower alkenyl has preferably from 2 to 7, especially from 2 to 4, carbon atoms and is preferably vinyl, prop-1-enyl or prop-2-enyl (allyl).

Lower alkenyloxy is, for example, vinyloxy, prop-1-enyloxy or prop-2-enyloxy (allyloxy).

Substituted lower alkyl $R_1$ or $R_2$ may carry one or more, but preferably not more than 3, substituents, which may be identical or different. Preferably, substituted lower alkyl $R_1$ or $R_2$ carries only one substituent.

Lower alkyl substituted by phenylamino or phenyl that is unsubstituted or substituted in the phenyl moiety by halogen, lower alkyl, hydroxy, lower alkanoyloxy, lower alkoxy, carboxy, lower alkoxycarbonyl, carbamoyl, N-lower alkyl-carbamoyl, N,N-di-lower alkyl-carbamoyl, cyano, amidino, amino, amino-lower alkyl, lower alkanoylamino, lower alkylamino, N,N-di-lower alkylamino or by trifluoromethyl is especially methyl substituted in that manner, and is preferably anilino-methyl or 4-methoxyanilino-methyl, or 3- or 4-aminophenyl-methyl.

Lower alkyl $R_1$ or $R_2$ substituted by a radical of the formula $R_5$—S(O$_q$)— wherein $R_5$ is lower alkyl and q is 0, 1 or 2 is especially methanesulfonyl-methyl.

An alkylene chain having from 2 to 5 carbon atoms that is formed by $R_1$ and $R_2$ together and is unsubstituted or substituted by lower alkyl is preferably propylene or butylene.

Preference is given to compounds of formula I wherein $R_1$ and $R_2$ are the other radicals mentioned with the exception of an unsubstituted or substituted alkylene chain.

Preferably the two radicals $R_1$ and $R_2$ are each independently of the other lower alkyl, or $R_2$ is unsubstituted or substituted phenyl, as defined above, while $R_1$ is hydrogen or also lower alkyl, especially methyl. In especially preferred compounds of formula I, $R_1$ is methyl and $R_2$ is methyl; or $R_1$ is hydrogen or also methyl and $R_2$ is phenyl that is unsubstituted or substituted especially by amino, nitro or by methoxy, especially 4-aminophenyl, 4-nitrophenyl or 4-methoxyphenyl.

In heterocyclyl of formula IA bonded via a ring nitrogen atom, m and n are each independently of the other from 0 to 3; preferably m is 0 or 1 and n is from 0 to 3; and especially: n+m=0 to 3, and more especially: m=0 and n=0 or 1.

Lower alkynyl is especially $C_2$–$C_7$alkynyl, preferably $C_2$–$C_4$alkynyl, such as ethynyl.

Tri-lower alkylsilanyl-lower alkynyl is especially trimethylsilanylethynyl.

Phenyl that is unsubstituted or substituted by halogen, nitro, trihalo-lower alkyl, hydroxy or by lower alkyl contains one or more, especially 3, but preferably one, of the mentioned substituents which can be selected independently of one another. Unsubstituted phenyl is preferred.

Thienyl is especially 2-thienyl.

Phenyl-lower alkoxy that is unsubstituted or substituted in the phenyl ring by halogen, nitro, trihalo-lower alkyl, hydroxy or by lower alkyl is especially benzyloxy.

Benzoylamino that is unsubstituted or substituted in the benzene ring by halogen, nitro, trihalo-lower alkyl, hydroxy or by lower alkyl is especially unsubstituted benzoylamino.

Monohalo-, dihalo- or trihalo-lower alkylcarbonylamino is especially trifluoroacetylamino.

Trihalo-lower alkanesulfonylamino is especially trifluoromethanesulfonylamino.

Lower alkylthio is especially methylthio.

Lower alkylsulfinyl (lower alkyl-(S=O)—) is especially methyl- or ethyl-sulfinyl.

Lower alkanesulfonyl is preferably methanesulfonyl.

Lower alkylenedioxy formed by two radicals $R_3$ together or two radicals $R_4$ together is preferably bonded to two vicinal ring atoms and is especially methylenedioxy. Lower alkylenedioxy is especially formed by two radicals $R_4$.

The ring marked A is a heterocyclyl having from 5 to 9 ring atoms and having at least one saturated bond, it being possible for a further ring hetero atom selected from O and S to be present in addition to the bonding nitrogen atom; preference is given to a corresponding 5-to 8-membered ring that does not contain a further hetero atom in addition to the bonding nitrogen atom, for example 2,3-dihydropyrrol-1-yl, 1,2,3,4-tetrahydropyridin-1-yl, 2,3,4,5-tetrahydroazepin-1-yl or 1,2,3,4,5,6-hexahydroazocin-1-yl.

The ring system marked B is a free or benzo-, thieno-, furo-, pyrrolo- or dihydropyrrolo-fused carbocyciic ring having from 5 to 9, preferably 6, carbon atoms that is fused to the ring A (via two vicinal atoms completing the ring) and may be unsaturated, partially saturated or fully saturated, and is especially benzo, naphtho, pyrrolo-fused benzo or 2,3-dihydropyrrolo-fused benzo.

Q is especially 2,3-dihydroindol-1-yl, 1,2,3,4-tetrahydroquinolin-1-yl, 2,3,4,5-tetrahydro-1H-benzo[b]azepin-1-yl, 1,2,3,4,5,6-hexahydrobenzo[b]azocin-1-yl, 2,3,6,7,8,9-hexahydro-1H-benzo [g]indol-1-yl, 1,2,3,5-tetrahydropyrrolo[2,3-f]indol-1-yl or 1,2,3,5,6,7-hexahydropyrrolo[2,3-f]indol-1-yl, each of which is unsubstituted or substituted by from 1 to 3 radicals $R_3$ or $R_4$ or $R_3$ and $R_4$ selected independently of one another from lower alkyl, N,N-di-lower alkylamino-lower alkyl, lower alkynyl, tri-lower alkylsilanyl-lower alkynyl, halogen, nitro, hydroxy, lower alkoxy, isothiocyanato, unsubstituted phenyl, unsubstituted phenyl-lower alkoxy, carboxy, lower alkoxycarbonyl, amino, azido, lower alkanoylamino, trihalo-lower alkylcarbonylamino, pyrrol-1-yl and pyrrolidin-1-yl or substituted by lower alkylenedioxy formed by two radicals $R_4$ together and is bonded to two vicinal ring atoms; Q is especially 2,3-dihydroindol-1-yl, 6-chloro-2,3-dihydroindol-1-yl, 6-bromo-2,3-dihydroindol-1-yl, 6-methyl-2,3-dihydroindol-1-yl or 1,2,3,4-tetrahydroquinolin-1-yl.

The bond marked by a parallel dotted line between the ring systems marked A and B is either a single bond or a double bond, preferably a double bond.

Salts of compounds of formula I are especially acid addition salts with organic or inorganic acids, especially the pharmaceutically acceptable, non-toxic salts. Suitable inorganic salts are, for example, carbonic acid (preferably in the form of carbonates or bicarbonates); hydrohalic acids, such as hydrochloric acid; sulfuric acid; or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, 2-hydroxybutyric acid, gluconic acid, glucosemonocarboxylic acid, fumaric acid, succinic acid, adipic acid, pimelic acid, suberic acid, azelaic acid, malic acid, tartaric acid, citric acid, glucaric acid, galactaric acid, amino acids, such as glutamic acid, aspartic acid, N-methylglycine, acetylaminoacetic acid, N-acetylasparagine or N-acetylcysteine, pyruvic acid, acetoacetic acid, phosphoserine, 2- or 3-glycerophosphoric acid, glucose-6-phosphoric acid, glucose-1-phosphoric acid, fructose-1,6-bisphosphoric acid, maleic acid, hydroxymaleic acid, methylmaleic acid, cyclohexanecarboxylic acid, adamantanecarboxylic acid, benzoic acid, salicylic acid, 1- or 3-hydroxynaphthyl-2-carboxylic acid, 3,4,5-trimethoxybenzoic acid, 2-phenoxybenzoic acid, 2-acetoxybenzoic acid, 4-aminosalicylic acid, phthalic acid, phenylacetic acid, mandelic acid, cinnamic acid, glucuronic acid, galacturonic acid, methane- or ethane-sulfonic acid, 2-hydroxyethanesulfonic acid, ethane-1,2-disulionic acid, benzenesulfonic acid, 2-naphthatenesulfonic acid, 1,5-naphthalene-disulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propylsulfamic acid, or other organic protonic acids, such as ascorbic acid.

Compounds of formula I that carry at least one free carboxy group can form internal salts or metal or ammonium salts, such as alkali metal or alkaline earth metal salts, for example sodium, potassium, magnesium or calcium salts or ammonium salts with ammonia or suitable organic amines, such as tertiary monoamines, for example triethylamine or tri(2-hydroxyethyl)amine, or heterocyclic bases, for example N-ethylpiperidine or N,N'-dimethyl-piperazine.

For the purposes of isolation or purification it is also possible to use pharmaceutically unacceptable salts, for example picrates or perchlorates. Only the salts that are pharmaceutically acceptable and non-toxic (at the doses in question) are used therapeutically and they are therefore preferred.

As a result of the close relationship between the novel compounds (especially of formula I) in free form and in the form of their salts, including those salts which can be used as intermediates, for example in the purification of the novel compounds or for the identification thereof, hereinabove and hereinbelow any reference to the free compounds should be understood as including also the corresponding salts, and solvates thereof, for example hydrates, as appropriate and expedient.

The compounds of formula I exhibit valuable pharmacologically acceptable properties. In particular, they exhibit specific inhibitory actions that are of pharmacological interest. They act especially as inhibitors of tyrosine protein kinase and/or (further) as inhibitors of serine/threonine protein kinases; they exhibit, for example, potent inhibition of the tyrosine kinase activity of the receptor for the epidermal growth factor (EGF) and the c-erbB2 kinase. Those receptor-specific enzyme activities play a key role in signal transmission in a large number of mammalian cells, including human cells, especially epithelial cells, cells of the immune system and cells of the central and peripheral nervous system. For example, the EGF-induced activation of the receptor-associated tyrosine protein kinase (EGF-R-PTK) in various cell types is a prerequisite for cell division and thus for the proliferation of the cell population. The administration of EGF-receptor-specific tyrosine kinase inhibitors therefore inhibits the reproduction of the cells. The same is true analogously of the other protein kinases mentioned hereinabove and hereinbelow.

The inhibition of the EGF-receptor-specific tyrosine protein kinase (EGF-R-PTK) can be demonstrated using known methods, for example using the receombinant intracellular domain of the EGF receptor (EGF-R ICD; see, for example, E. McGlynn et al., Europ. J. Biochem. 207, 265–275 (1992)). The compounds of formula I inhibit the enzyme activity in comparison with the control without inhibitor by 50% ($IC_{50}$), for example in a concentration of from 0.001 to 20 $\mu$M, especially from 0.01 to 5 $\mu$M.

The action of the compounds of formula I on the EGF-stimulated cellular tyrosine phosphorylation in the EGF receptor can be determined in the human A431 epithelium carcinoma cell line by means of an ELISA that is described in U. Trinks et al., J. Med. Chem. 37(7), 1015–1027 (1994). In that test (EGFR-ELISA) the compounds of formula I exhibit inhibition at concentrations in the nanomolar to micromolar range.

The stimulation of dormant BALB/c3T3 cells by EGF rapidly induces the expression of c-fos mRNA. Pretreatment of the cells with a compound of formula I prior to the stimulation with EGF can inhibit the c-fos expression. That test procedure is likewise described in U. Trinks et a., J. Med. Chem. 37(7), 1015–1027 (1994).

In the micromolar range also, the compounds of formula I also exhibit, for example, inhibiton of the cell growth of EGF-dependent cell lines, for example the epidermoid BALB/c mouse keratinocyte cell line (see Weissmann, B. A., and Aaronson, S. A., Cell 32, 599 (1983)) or the A431 cell line, which are acknowledged as useful standard sources of EGF-dependent epithelial cells (see Carpenter, G., and Zendegni, J. Anal. Biochem. 153, 279–282 (1985)). In a known test method (see Meyer et al., Int. J. Cancer 43, 851 (1989)) the inhibitory action of the compounds of formula I is determined briefly as follows: BALB/MK cells (10 000/ microtiter plate well) are transferred to 96-well microtiter plates. The test compounds (dissolved in DMSO) are added in a series of concentrations (dilution series), so that the final concentration of DMSO is no greater than 1% (v/v). After the addition, the plates are incubated for three days, during which time the control cultures without test compound are able to undergo at least three cell division cycles. The growth of the MK cells is measured by means of methylene blue staining: after the incubation the cells are fixed with glutaraldehyde, washed with water and stained with 0.05% methylene blue. After a washing step, the stain is eluted with 3% HCl and the optical density per well of the microtitre plate is measured using a Titertek multiskan at 665 nm. $IC_{50}$ values are determined by means of a computer-aided system using the formula $$IC_{50}=[(OD_{test}-OD_{start})/(OD_{control}-OD_{start})]\times 100.$$

The $IC_{50}$ value in those experiments is defined as that concentration of the test compound in question which results in a 50% decrease in the number of cells in comparison with the control without inhibitor. The compounds of formula I exhibit inhibitory actions in the micro-molar range, especially having an $IC_{50}$ of approximately from 0.1 to 50 $\mu$M.

The compounds of formula I are also capable of inhibiting the growth of tumor cells in vivo, as shown, for example, by the test described below: the test is based on the inhibition of the growth of the human epidermoid carcinoma A431 (ATCC No. CRL 1555; American Type Culture Collection, Rockville, Md., USA; see Santon, J. B., et al., Cancer Research 46, 4701–4705 (1986) and Ozawa, S., et al, Int. J. Cancer 40, 706–710 (1987)), which is transplanted into female BALB/c naked mice (Bomholtgard, Denmark). That carcinoma exhibits a growth which correlates with the extent of the expression of the EGF receptor. In the experiment, tumors of about 1 $cm^3$ volume grown in vivo are surgically removed from experimental animals under sterile conditions. Those tumors are comminuted and suspended in 10 volumes (w/v) of phosphate-buffered saline. The suspension is injected s.c. into the left flank of the animals (0.2 ml/mouse in phosphate-buffered saline). Alternatively, $1\times 10^6$ cells from an in vitro culture in 0.2 ml of phosphate-buffered saline can be injected. The treatment with the test compounds of formula I is begun 5 or 7 days after transplantation when the tumors have attained a diameter of 4–5 mm. The test compound in question is administered (in different doses for different groups of animals) once daily for 15 successive days. The tumor growth is determined by measuring the diameter of the tumors along three axes that are perpendicular to one another. The tumor volumes are calculated using the known formula $p\times L\times D^2/6$ (see Evans, B. D., et al., Brit. J. Cancer 45, 466–468 (1982)). The results are expressed as treatment/control percentages (T/C×100= T/C % ).

In addition to or instead of inhibiting the EGF receptor tyrosine protein kinase, the compounds of formula I also inhibit other tyrosine protein kinases that are involved in the signal transmission mediated by trophic factors, for example the abl kinase, such as especially the v-abl kinase ($IC_{50}$, for example, from 0.01 to 5 $\mu$M), kinases of the src kinase family, such as especially the c-src kinase ($IC_{50}$, for example, from 0.01 to 10 $\mu$M), and also lck and fyn; other kinases of the EGF family, for example the c-erbB2 kinase (HER-2), the c-erbB3 kinase, the c-erbB4 kinase; members of the PDGF tyrosine protein kinase family, for example the PDGF receptor, CSF-1, Kit, VEGF-R and FGF-R; and the insulin-like growth factor receptor kinase (IGF-1-kinase), and also serine/threonine kinases, for example protein kinase C, all of which play a part in growth regulation and transformation in mammal cells, including human cells. Finally, the compounds of formula I can also be used in the inhibition of angiogenesis.

The above-mentioned inhibition of the v-abl tyrosine kinase is determined in accordance with the methods of N. Lydon et at, Oncogene Research 5, 161–173 (1990) and J. F. Geissler et al., Cancer Research 52, 4492–4498 (1992), with [$Val^5$]-angiotensin II and [$_\gamma-^{32}P$]-ATP being used as substrates.

The inhibition of the c-erbB2 tyrosine kinase (HER-2) can be determined, for example, analogously to the method used for EGF-R-PTK (see C. House et al., Europ. J. Biochem. 140, 363–367 (1984)). The c-erbB2 kinase can be isolated and its activity determined in accordance with protocols known per se, for example according to T. Akiyama et at., Science 232, 1644 (1986)).

The compounds of formula I that inhibit the tyrosine kinase activity of the receptor for the epidermal growth factor (EGF) or, further, the other tyrosine protein kinases mentioned or also serine/threonine kinases can therefore be used, for example, in the treatment of benign or malignant tumors (for example carcinoma of the kidneys, liver, adrenal glands, bladder, breast, stomach, ovaries, colon, rectum, prostate, pancreas, lungs, vagina or thyroid, sarcoma, glioblastomas and numerous tumors of the neck and head). They are able to bring about the regression of tumors and to prevent the formation of tumor metastases and the growth of (also micro-)metastases. More especially they can be used in epidermal hyperproliferation (psoriasis), in prostate hyperplasia, in the treatment of neoplasias, especially of epithelial character, for example mammary carcinoma, and in leukemias. It is also possible to use the compounds of formula I in the treatment of diseases of the immune system insofar as several or, especially, individual tyrosine protein kinases and/or (further) serine/threonine protein kinases are involved; the compounds of formula I can be used also in the treatment of diseases of the central or peripheral nervous system where signal transmission by at least one tyrosine protein kinase and/or (further) serine/threonine protein kinase is involved.

Generally the present invention relates also to the use of the compounds of formula I in the inhibition of the said protein kinases.

The compounds according to the invention can be used both on their own and in combination with other pharmacologically active substances, for example together with inhibitors of enzymes of polyamine biosynthesis, inhibitors of protein kinase C, inhibitors of other tyrosine kinases, cytokines, negative growth regulators, for example TGF-β or IFN-β, aromatase inhibitors, antioestrogens and/or cytostatics.

In the preferred subjects of the invention mentioned below, where appropriate and expedient it is possible to use the more specific definitions mentioned at the beginning in place of more general definitions.

Preference is given to a compound of formula I wherein
$R_1$ and $R_2$ are each independently of the other lower alkyl; monohalo-, dihalo- or trihalo-lower alkyl; lower alkoxy; phenyl that is unsubstituted or substituted by halogen, monohalo-, dihalo- or trihalo-lower alkyl, carbamoyl-methoxy, carboxy-methoxy, benzyloxycarbonyl-methoxy, lower alkoxycarbonyl-methoxy, phenyl, amino, amino-lower alkyl, lower alkanoylamino, lower alkoxycarbonylamino, phenyl-lower alkoxycarbonylamino, furoyl, thienylcarbonyl, N-lower alkylamino, N,N-di-lower alkylamino, hydroxy, lower alkoxy, lower alkanoyloxy, carboxy, lower alkoxycarbonyl, carbamoyl, N-lower alkyl-carbamoyl, N,N-di-lower alkyl-carbamoyl, cyano, amidino, N-(N',N'-di-lower alkylaminomethylidene)-amino, N-((N',N'-di-lower alkylamino)-(lower alkyl)-methylidene)-amino, guanidino, ureido, $N^3$-lower alkylureido, $N^3,N^3$-di-lower alkylureido, thioureido, $N^3$-lower alkylthioureido, $N^3,N^3$-di-lower alkylthioureido, lower alkanesulfonylamino, benzene- or naphthalene-sulfonylamino that is unsubstituted or lower alkyl-substituted at the benzene or naphthalene ring, azido or by nitro; hydrogen; unsubstituted or halo- or lower alkyl-substituted pyridyl; N-benzyl-pyridonium; naphthyl; cyano; carboxy; lower alkoxycarbonyl; carbamoyl; N-lower alkyl-carbamoyl; N,N-di-lower alkyl-carbamoyl; N-benzyl-carbamoyl; formyl; lower alkanoyl; lower alkenyl; lower alkenyloxy; or lower alkyl substituted by halogen, amino, lower alkylamino, piperazino, di-lower alkylamino, phenylamino or phenyl (each unsubstituted or substituted in the phenyl moiety by halogen, lower alkyl, hydroxy, lower alkanoyloxy, lower alkoxy, carboxy, lower alkoxycarbonyl, carbamoyl, N-lower alkyl-carbamoyl, N,N-di-lower alkyl-carbamoyl, cyano, amidino, amino, amino-lower alkyl, lower alkanoylamino, lower alkylamino, N,N-di-lower alkylamino or by trifluoromethyl), hydroxy, lower alkoxy, cyano, carboxy, lower alkoxycarbonyl, carbamoyl, N-lower alkyl-carbamoyl, N,N-di-lower alkyl-carbamoyl, mercapto or by a radical of the formula $R_5$—$S(O_q)$— wherein $R_5$ is lower alkyl and q is 0, 1 or 2, and Q is a radical of formula IA selected from 2,3-dihydroindol-1-yl; and preferably 1,2,3,4-tetrahydroquinolin-1-yl, 2,3,4,5-tetrahydro-1H-benzo[b]azepin-1-yl, 1,2,3,4,5,6-hexahydrobenzo-[b]azocin-1-yl, 2,3,6,7,8,9-hexahydro-1H-benzo[g]indol-1-yl, 1,2,3,5-tetrahydropyrrolo-[2,3-f]indol-1-yl and 1,2,3,5,6,7-hexahydro-pyrrolo[2,3-f]indol-1-yl; each of the mentioned radicals being unsubstituted or substituted by from 1 to 3 (i.e. m+n=0 to 3) radicals $R_3$ or $R_4$ or $R_3$ and $R_4$ selected independently of one another from lower alkyl, N,N-di-lower alkylamino-lower alkyl, lower alkynyl, tri-lower alkylsilanyl-lower alkynyl, halogen, nitro, hydroxy, lower alkoxy, isothiocyanato, unsubstituted phenyl, unsubstituted phenyl-lower alkoxy, carboxy, lower alkoxycarbonyl, amino, azido, lower alkanoylamino, trihalo-lower alkylcarbonylamino, pyrrol-1-yl and pyrrolidin-1-yl or substituted by lower alkylenedioxy that is formed by two radicals $R_4$ together and is bonded to two vicinal ring atoms; Q is especially 2,3-dihydroin-dol-1-yl, 6-chloro-2,3-dihydroindol-1-yl, 6-bromo-2,3-dihydroindol-1-yl, 6-methyl-2,3-dihydro-indol-1-yl or more especially 1,2,3,4-tetrahydroquinolin-1-yl;

or a salt thereof where at least one salt-forming group is present.

Great preference is given to a compound of formula I wherein
$R_1$ and $R_2$ are each independently of the other selected from hydrogen, lower alkyl, such as methyl, and phenyl that is unsubstituted or substituted by halogen, monohalo-, dihalo- or trihalo-lower alkyl, carbamoyl-methoxy, carboxy-methoxy, benzyloxycarbonyl-methoxy, lower alkoxycarbonyl-methoxy, phenyl, amino, amino-lower alkyl, lower alkanoylamino, lower alkoxycarbonylamino, phenyl-lower alkoxycarbonylamino, furoyl, thienylcarbonyl, N-lower alkylamino, N,N-di-lower alkylamino, hydroxy, lower alkanoyloxy, carboxy, lower alkoxycarbonyl, carbamoyl, N-lower alkyl-carbamoyl, N,N-di-lower alkyl-carbamoyl, cyano, amidino, N-(N',N'-di-lower alkylaminomethylidene)-amino, N-((N',N'-di-lower alkylamino)-(lower alkyl)-methylidene)amino, guanidino, ureido, $N^3$-lower alkylureido, $N^3,N^3$-di-lower alkylureido, thioureido, $N^3$-lower alkylthioureido, $N^3,N^3$-di-lower alkylthioureido, lower alkanesulfonylamino, benzene- or naphthalene-sulfonylamino that is unsubstituted or lower alkyl-substituted at the benzene or naphthalene ring, azido or by nitro, and Q is a radical of formula IA selected from 2,3-dihydroindol-1-yl; and preferably 1,2,3,4-tetrahydroquinolin-1-yl, 2,3,4,5-tetrahydro-1H-benzo[b]azepin-1-yl, 1,2,3,4,5,6-hexahydrobenzo-[b]azocin-1-yl, 2,3,6,7,8,9-hexahydro-1H-benzo[g]indol-1-yl, 1,2,3,5-tetrahydropyrrolo-[2,3-f]indol-1-yl and 1,2,3,5,6,7-hexahydro-pyrrolo[2,3-f]indol-1-yl; each of the mentioned radicals being unsubstituted or substituted by from 1 to 3 radicals $R_3$ or $R_4$ or $R_3$ and $R_4$ selected independently of one another from lower alkyl, N,N-di-lower alkylamino-lower alkyl, lower alkynyl, tri-lower alkylsilanyl-lower alkynyl, halogen, nitro, hydroxy, lower alkoxy, isothiocyanato, unsubstituted phenyl, unsubstituted phenyl-lower alkoxy, carboxy, lower alkoxycarbonyl, amino, azido, lower alkanoylamino, trihalo-lower alkylcarbonylamino, pyrrol-1-yl and pyrrolidin-1-yl or substituted by lower alkylenedioxy that is formed by two radicals $R_4$ together and is bonded to two vicinal ring atoms; Q is especially 2,3-dihydroindol-1-yl, 6-chloro-2,3-dihydroindol-1-yl, 6-bromo-2,3-dihydroindol-1-yl, 6-methyl-2,3-dihydroindol-1-yl especially 1,2,3,4-tetrahydroquinolin-1-yl;

or a salt thereof.

Special preference is given to a compound of formula I wherein
either the two radicals $R_1$ and $R_2$ are each independently of the other lower alkyl, preferably each methyl;
or $R_1$ is hydrogen and $R_2$ is phenyl that is unsubstituted or especially substituted by amino, nitro or by methoxy, especially 4-aminophenyl, 4-nitrophenyl or 4-methoxyphenyl; and Q is 2,3-dihydroindol-1-yl, 6-chloro-2,3-dihydroindol-1-yl, 6-bromo-2,3-dihydroindol-1-yl, 6-methyl-2,3-dihydroindol-1-yl or especially 1,2,3,4-tetrahydroquinolin-1-yl;

or a salt thereof.

Greatest preference is given to the compounds of formula I described in the Examples and the pharmaceutically acceptable salts thereof.

The compounds of formula I and their salts are prepared in accordance with processes known per se. The process according to the invention is as follows:

a) a pyrrolo[2,3-d]pyrimidine derivative of formula II

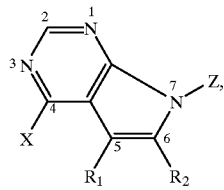

(II)

wherein X is a suitable leaving group, Z is hydrogen or 1-aryl-lower alkyl and the other substituents are as defined above for compounds of formula I, free functional groups present in the radicals $R_1$ and $R_2$ being protected if necessary by readily removable protecting groups, is reacted with an aza compound of formula III

Q—H     (III), wherein Q is as defined above for compounds of formula I, free functional groups present in the radical Q being protected if necessary by readily removable protecting groups, and any protecting groups and, if present, the 1-aryl-lower alkyl radical Z are removed, or b) a pyrrolo[2,3-d]pyrimidin-4-one derivative of formula IV

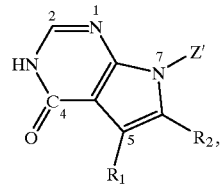

(IV)

wherein Z' is 1-aryl-lower alkyl and $R_1$ and $R_2$ are as defined above for compounds of formula I, free functional groups present in the radicals $R_1$ and $R_2$ being protected if necessary by readily removable protecting groups, is reacted in the presence of a dehydrating agent and a tertiary amine (which is preferably in the form of a salt with a strong acid) with an aza compound of the above formula III and any protecting groups present are removed;

and, if desired, after carrying out one of the process variants a) and b), a compound of formula I is converted into a different compound of formula I; and/or, if necessary for the preparation of a salt, a resulting free compound of formula I is converted into a salt or, if necessary for the preparation of a free compound, a resulting salt of a compound of formula I is converted into the free compound; or an obtainable salt of a compound of formula I is converted into a different salt of a compound of formula I.

DETAILED DESCRIPTION OF THE PREFERRED PROCESS STEPS

The above processes are described in more detail below (see also German Offenlegungsschrift No. 30 36 390, published on May 13th 1982, and A. Jorgensen et at, J. Heterocycl. Chem. 22, 859 [1985]). In the following more detailed description, unless otherwise indicated the radicals $R_1$, $R_2$, Q, $R_3$ and $R_4$ and the variables m and n are as defined for compounds of formula I General Remarks:

The end products of formula I may contain substituents that can be used also as protecting groups in starting materials for the preparation of other end products of formula 1. Within the scope of this text, unless the context indicates otherwise the term "protecting group" is therefore used to denote only a readily removable group that is not a constituent of the desired end product of formula I in question.

Process a)

In the compound of formula II, a suitable leaving group X is preferably halogen, such as bromine, iodine or especially chlorine. 1-Aryl-lower alkyl Z is preferably 1-phenyl-lower alkyl, such as especially 1-phenylethyl or more especially benzyl.

Free functional groups present in the radicals $R_1$ and $R_2$ and also Q, which are if necessary protected by readily removable protecting groups, are especially amino or lower alkylamino, or also hydroxy.

Protecting groups and the methods by which they are introduced and removed are described, for example, in "Protective Groups in Organic Chemistry", Plenum Press, London, New York 1973, and in "Methoden der organischen Chemie", Houben-Weyl, 4th edition, Vol. 15/1, Georg-Thieme-Verlag, Stuttgart 1974, and in Theodora W. Greene, "Protective Groups in Organic Synthesis, John Wiley & Sons, New York 1981. It is characteristic of protecting groups that they can be removed readily, that is to say without undesirable secondary reactions taking place, for example by solvolysis, reduction, photolysis or under physiological conditions.

A protected amino group may be, for example, in the form of a readily cleavable acylamino, arylmethylamino, etherified mercaptoamino or 2-acyl-lower alk-1-enylamino group.

In such an acylamino group, acyl is, for example, the acyl radical of an organic carboxylic acid having, for example, up to 18 carbon atoms, especially an unsubstituted or substituted, for example halo- or aryi-substituted, alkanecarboxylic acid or an unsubstituted or substituted, for example halo-, lower alkoxy- or nitro-substituted, benzoic acid, or a carbonic acid semiester. Such acyl groups are, for example, lower alkanoyl, such as formyl, acetyl or propionyl, halo-lower alkanoyl, such as 2-haloacetyl, especially 2-chloro-, 2-bromo-, 2-iodo-, 2,2,2-trifluoro- or 2,2,2-trichloro-acetyl, unsubstituted or substituted, for example halo-, lower alkoxy- or nitro-substituted, benzoyl, for example benzoyl, 4-chlorobenzoyl, 4-methoxybenzoyl or 4-nitrobenzoyl, or lower alkoxycarbonyl that is branched in the 1-position of the lower alkyl radical or suitably substituted in the 1- or 2-position, especially tert-lower alkoxycarbonyl, for example tert-butoxycarbonyl, arylmethoxycarbonyl having one or two aryl radicals which are preferably phenyl that is unsubstituted or mono- or poly-substituted, for example, by lower alkyl, especially tert-lower alkyl, such as tert-butyl, lower alkoxy, such as methoxy, hydroxy, halogen, such as chlorine, and/or by nitro, such as unsubstituted or substituted benzyloxycarbonyl, for example 4-nitrobenzyloxycarbonyl, or substituted diphenylmethoxycarbonyl, for example benzhydryloxycarbonyl or di(4-methoxyphenyl)-methoxycarbonyl, aroylmethoxycarbonyl wherein the aroyl group is preferably benzoyl that is unsubstituted or substituted, for example, by halogen, such as bromine, for example phenacyloxycarbonyl, 2-halo-lower alkoxycarbonyl, for example 2,2,2-trichloro-ethoxycarbonyl, 2-bromoethoxycarbonyl or 2-iodoethoxycarbonyl, or 2-(trisubstituted sityl)-ethoxycarbonyl wherein the substituents are each independently of the others an unsubstituted or substituted, for example lower alkyl-, lower alkoxy-, aryl-, halo- or nitro-substituted, aliphatic, araliphatic, cycloaliphatic or aromatic hydrocarbon radical having up to 15 carbon atoms, such as corresponding unsubstituted or substituted lower alkyl, phenyl-lower alkyl, cycloalkyl or phenyl, for example 2-tri-lower alkylsilyl-ethoxycarbonyl, such as 2-trimethylsilylethoxycarbonyl or 2-(di-n-butyl-methyl-silyl)-ethoxycarbonyl, or 2-triarylsilyl-ethoxycarbonyl, for example 2-triphenylsilylethoxycarbonyl.

In an arylmethylamino group, which is a mono-, di- or especially tri-arylmethylamino group, the aryl radicals are especially unsubstituted or substituted phenyl radicals. Such groups are, for example, benzyl-, diphenylmethyl- or especially trityl-amino.

An etherified mercapto group in an amino group protected by such a radical is especially arylthio or aryl-lower alkylthio wherein aryl is especially phenyl that is unsubstituted or substituted, for example by lower alkyl, such as methyl or tert-butyl, lower alkoxy, such as methoxy, halogen, such as chlorine, and/or by nitro. One such amino-protecting group is, for example, 4-nitrophenylthio.

In a 2-acyl-lower alk-1-en-1-yl radical that can be used as an amino-protecting group, acyl is, for example, the corresponding radical of a lower alkanecarboxylic acid, of a benzoic acid that is unsubstituted or substituted, for example, by lower alkyl, such as methyl or tert-butyl, lower alkoxy, such as methoxy, halogen, such as chlorine, and/or by nitro, or especially of a carbonic acid semiester, such as a carbonic acid lower alkyl semiester. Such protecting groups are especially 1-lower alkanoyl-prop-1-en-2-yl, for example 1-acetyl-prop-1-en-2-yl, or 1-lower alkoxycarbonyl-prop-1-en-2-yl, such as 1-ethoxycarbonyl-prop-1-en-2-yl.

Preferred amino-protecting groups are acyl radicals of carbonic acid semiesters, especially tert-butyloxycarbonyl, benzyloxycarbonyl that is unsubstituted or substituted, for example as indicated, for example 4-nitro-benzyloxycarbonyl, or diphenylmethoxycarbonyl, or 2-halo-lower alkoxycarbonyl, such as 2,2,2-trichloroethoxycarbonyl, and also trityl or formyl.

The reaction between the derivative of formula II and the aza compound of formula III is effected in suitable, inert polar solvents, especially alcohols, for example lower alkanols, such as methanol, propanol, isopropanol or especially ethanol or n-butanol. In some cases, the addition of a solubilizer, such as 1,3-dimethyl-3,4,5,6-tetrahydro-2(1H)-pyrimidinone (DMPU), is advantageous. The reaction is effected at elevated temperatures, for example in a temperature range of from 70 to 150° C., preferably under reflux conditions. For the preparation of those compounds where a sterically hindered compound (for example a 2-lower alkyl-indoline) of formula III is used, it is preferable to use tert-butanol or an aprotic solvent, such as dimethylformamide, dimethylacetamide or N-methylpyrrolidin-2-one, as solvent. If necessary, a base is added, for example an alkali metal or alkaline earth metal carbonate or hydroxide, or a tertiary nitrogen base, such as pyridine, 2,6-lutidine, collidine, N-methyl-morpholine, triethylamine, diisopropylethylamine, 4-dimethylaminopyridine or N,N-dimethyl-aniline.

If Z in the compound of formula II is 1-aryl-lower alkyl, that radical is removed in the resulting precursor of the compound of formula I (with Z in place of the hydrogen atom at the nitrogen atom). That is effected, for example, by treatment with protonic acids, such as hydrochloric acid, phosphoric acid or polyphosphoric acid, at preferred temperatures of from 20° C. to 150° C. and optionally in the presence of water (this is especially the preferred method for Z=1-phenylethyl); or preferably by treatment with Lewis acids, especially AlCl$_3$, in an aromatic solvent, especially in benzene and/or toluene, at elevated temperature, especially under reflux [this is especially the preferred variant for Z=benzyl; see also the analogous procedure in Chem. Pharm. Bull. 39(5), 1152 (1991)].

Removal of Protecting Groups

The removal of protecting groups that are not constituents of the desired end product of formula I is carried out in a manner known per se, for example by means of solvolysis, especially hydrolysis, alcoholysis or acidolysis, or by means of reduction, especially hydrogenolysis or chemical reduction, optionally stepwise or simultaneously. The removal is effected preferably in accordance with or analogously to the methods described in the standard works mentioned above.

A protected amino group, for example, is freed in a manner known per se and, according to the nature of the protecting groups, in various ways, preferably by solvolysis or reduction. 2-Halo-lower alkoxycarbonylamino (where appropriate after conversion of a 2-bromo-lower alkoxycarbonylamino group into a 2-iodo-lower alkoxycarbonylamino group), aroylmethoxycarbonylamino or 4-nitrobenzyloxycarbonylamino can be cleaved, for example, by treatment with a suitable chemical reducing agent, such as zinc in the presence of a suitable carboxyiic acid, such as aqueous acetic acid. Aroylmethoxycarbonylamino can be cleaved also by treatment with a nucleophilic, preferably salt-forming, reagent, such as sodium thiophenolate, and 4-nitrobenzyloxycarbonylamino also by treatment with an alkali metal dithionite, for example sodium dithionite. Unsubstituted or substituted diphenylmethoxycarbonylamino, tert-lower alkoxycarbonylamino or 2-trisubstituted silylethoxycarbonylamino can be cleaved by treatment with a suitable acid, for example formic acid or trifluoroacetic acid; unsubstituted or substituted benzyloxycarbonylamino can be cleaved, for example, by means of hydrogenolysis, i.e. by treatment with hydrogen in the presence of a suitable hydrogenation catalyst, such as a palladium catalyst; unsubstituted or substituted triarylmethylamino or formylamino can be cleaved, for example, by treatment with an acid, such as a mineral acid, for example hydrochloric acid, or an organic acid, for example formic, acetic or trifluoroacetic acid, where appropriate in the presence of water, and an amino group protected by an organic silyl group can be freed, for example, by means of hydrolysis or alcoholysis. An amino group protected by 2-haloacetyl, for example 2-chloroacetyl, can be freed by treatment with thiourea in the presence of a base, or with a thiolate salt, such as an alkali metal thiolate, of thiourea and subsequent solvolysis, such as alcoholysis or hydrolysis, of the resulting condensation product. An amino group protected by 2-substituted silylethoxycarbonyl can be converted into the free amino group also by treatment with a salt of hydrofluoric acid that yields fluoride anions.

Process b)

1-Aryl-lower alkyl Z' in a compound of formula IV is especially 1-phenylethyl and also benzyl.

The compound of formula IV is in tautomeric equilibrium (lactam/lactim form), it being assumed that the lactam form (formula IV) predominates. Formula IV is used to represent the two possible forms of equilibrium.

The lactim form has the formula IVa

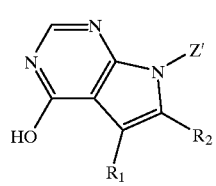

(IVa)

wherein the substituents are as defined for compounds of formula IV.

The dehydrating agent used is especially a strong chemical dehydrating agent, more especially phosphorus pentoxide ($P_4O_{10}$).

A suitable tertiary amine is especially ammonia substituted by three radicals selected independently of one another from alkyl, especially lower alkyl, such as methyl or ethyl, and cycloalkyl having from 3 to 7 carbon atoms, especially cyclohexyl, for example N,N-di-methyl-N-cyclohexylamine, N-ethyl-N,N-diisopropylamine or triethylamine, or also pyridine, N-methylmorpholine or 4-dimethylaminopyridine.

The tertiary amine is preferably in the form of a salt with a strong acid, preferably an inorganic acid, such as sulfuric acid, phosphoric acid or especially a hydrogen halide, such as hydrogen chloride.

The reaction between the pyrrolo-pyrimidinone of formula IV and the aza compound of formula III is effected at elevated temperature, for example at from 200 to 250° C.

Additional Process Steps

In the additional process steps, which are optional, functional groups of the starting compounds that are not intended to participate in the reaction may be unprotected or may be in protected form; for example they may be protected by one or more of the protecting groups mentioned above. The protecting groups may be removed from the end products, simultaneously or in sequence, in accordance with one of the methods mentioned under the heading "Removal of protecting groups".

The conversion of a compound of formula I into a different compound of formula I is effected especially by conversion of substituents in formula I.

For example, for the preparation of a compound of formula I wherein $R_1$ is dimethylaminomethyl and the other substituents are as defined above for compounds of formula I, a compound corresponding to formula I wherein $R_1$ is hydrogen and other substituents are as defined above for compounds of formula I, any further free functional groups present being protected if necessary by readily removable protecting groups, can be reacted with N,N-di-methyl-methyleneimmonium iodide and any protecting groups present removed. The reaction is carried out with the exclusion of moisture in a suitable inert solvent, for example a suitable ether, such as a cyclic ether, such as especially tetrahydrofuran, at elevated temperature, preferably under reflux.

For the preparation of a compound of formula I wherein at least one of the radicals $R_1$ and $R_2$ is hydroxy-substituted phenyl and/or wherein at least one of the radicals $R_3$ and $R_4$ is hydroxy and the other substituents are as defined above for compounds of formula I, it is also possible for a compound corresponding to formula I wherein at least one of the radicals $R_1$ and $R_2$ is lower alkoxy-substituted, especially methoxy-substituted, phenyl and/or wherein at least one of the radicals $R_3$ and $R_4$ is lower alkoxy and the other substituents are as defined above for compounds of formula I, any free functional groups present being protected if necessary by readily removable protecting groups, to be reacted with boron tribromide or aluminum(III) chloride, and any protecting groups present to be removed. The reaction is carried out with the exclusion of moisture in a suitable inert solvent, for example a suitable halogenated hydrocarbon, such as especially methylene chloride, at temperatures of approximately from −20° C. to +50° C., preferably with ice-cooling or at room temperature.

For the preparation of a compound of formula I wherein at least one of the radicals $R_1$ and $R_2$ is amino-substituted amino and/or wherein at least one of the radicals $R_3$ and $R_4$ is amino and the other substituents are as defined above for compounds of formula I, a compound of formula I wherein at least one of the radicals $R_1$ and $R_2$ is nitro-substituted phenyl and/or wherein at least one of the radicals $R_3$ and $R_4$ is nitro and the other substituents are as defined above for compounds of formula I, any free functional groups present being protected if necessary by readily removable protecting groups, can be catalytically hydrogenated and any protecting groups present removed. The hydrogenation is preferably carried out under elevated pressure or especially at normal pressure in the presence of a suitable hydrogenation catalyst, such as especially Raney nickel, in an inert solvent or solvent mixture, such as especially a mixture of a suitable cyclic ether and a suitable lower alkanol, such as preferably a mixture of tetrahydrofuran and methanol, at temperatures of approximately from 0° C. to +50° C., preferably at room temperature.

For the preparation of a compound of formula I wherein at least one of the radicals $R_1$ and $R_2$ is phenyl substituted by N-(N',N'-di-lower alkylaminomethylidene)-amino or by N-((N',N'-di-lower alkylamino)-(lower alkyl)-methylidene) amino and the other substituents are as defined above for compounds of formula I, a compound corresponding to formula I wherein at least one of the radicals $R_1$ and $R_2$ is amino-substituted phenyl and the other substituents are as defined above for compounds of formula I, any further free functional groups present being protected if necessary by readily removable protecting groups, can be reacted with a N,N-di-lower alkylformamide diethylacetal, especially N,N-dimethylformamide dimethylacetal, or N,N-di-lower alkyl-lower alkylcarboxylic acid amide diethylacetal, especially N,N-dimethylacetamide dimethylacetal, in an inert solvent, for example in toluene, and any protecting groups present removed.

Lower alkyl $R_1$ or $R_2$ substituted by a radical of the formula $R_5$—S($O_q$)—, wherein $R_5$ is lower alkyl and q is 0, or lower alkylthio $R_3$ or $R_4$ can be converted into corresponding $R_5$—S($O_q$)—wherein q is 1 or 2, that is into lower alkylsulfinyl or lower alkanesulfonyl, respectively, by oxidizing the corresponding thio compounds, for example with hydrogen peroxide, a peracid, such as 3-chloroperbenzoic acid, performic acid or peracetic acid, an alkali metal peroxysulfate, such as potassium peroxymonophosphate, chromium trioxide or gaseous oxygen in the presence of platinum. The oxidation is carried out under conditions that are as mild as possible, using the stoichiometric amount of the oxidizing agent in order to avoid overoxidation. Suitable solvents are especially methylene chloride, chloroform, acetone, tetrahydrofuran or tert-butyl methyl ether, and the temperature is preferably from −30 to 50° C., preferably in the range of from 18 to 28° C., for example at room temperature. For the preparation of sulfinyl compounds it is possible to use, preferably, milder oxidizing agents, such as sodium or potassium metaperiodate, in a polar solvent, such as acetic acid or ethanol.

From compounds of formula I wherein $R_1$ and/or $R_2$ is phenyl substituted by cyano or by cyano-$C_1$–$C_6$alkyl it is possible to obtain the corresponding cyano-lower alkylphenyl compound by reduction, for example by catalytic hydrogenation, for example in the presence of Raney nickel or especially Raney-Ushibara nickel, in an alcohol, such as methanol, at preferred temperatures of from 20 to 100° C., preferably at about 90° C., elevated hydrogen pressures, for example from 1 to 15 MPa (about 10 to 150 atm), being preferred, or with a suitable complex hydride, such as lithium aluminum hydride in a suitable solvent, especially an ether, such as diethyl ether, preferably under reflux.

From compounds of formula I wherein $R_1$ and/or $R_2$ is cyano-substituted phenyl it is possible to obtain the corresponding amidines by aminolysis with ammonia or by a Pinner cleavage via the formation of imino esters (alkyl imidates) by the addition of dry hydrogen chloride to a mixture of the nitrile starting material and an alcohol and subsequent treatment with ammonia (see Chem. Ber. 10, 1889 (1877); Chem. Ber. 11, 4, 1475 (1878) or Chem. Ber. 16, 352, 1643 (1883)).

From compounds of formula I wherein $R_1$ and/or $R_2$ is amino-substituted lower alkyl or amino-substituted phenyl it is possible to obtain by acylation the corresponding compounds wherein the place of one or more of the amino groups has been taken by lower alkanoyl-amino or (in the case of amino-substituted phenyl as starting material) ureido, $N^3$-lower alkylureido, $N^3,N^3$-di-lower alkylureido, lower alkanesulfonylamino, or benzene- or naphthalenesulfonylamino that is unsubstituted or lower alkyl-substituted at the benzene or naphthalene ring, by acylation under customary conditions. A suitable acylating agent is, for example, any corresponding suitable reagent that is suitable for the acylation of amino groups, for example a corresponding acyl halide, such as a bromide or chloride, a corresponding anhydride or mixed anhydride, a cyanate (for the preparation of ureido compounds), for example a corresponding alkali metal cyanate, or an isocyanate. N-Sulfonylation can be carried out with corresponding sulfonyl halides or anhydrides. The reactions take place in a solvent inert towards the reaction and at preferred temperatures in the range of from −20 to approximately 120° C., preferably at about room temperature.

For the conversion of hydroxy into carbamoyl or into carbamoyl substituted as indicated in the substituent definitions given above or into lower alkanoyloxy, corresponding acylating agents are suitable, for example corresponding halides, anhydrides or mixed anhydrides.

The reaction conditions are analogous to those given above for the acylation of amino groups. Acylation in situ, for example in the presence of condensation agents, such as carbodiimides, is also possible. For the introduction of carbamoyl or substituted carbamoyl it is also possible to use corresponding cyanates or alkyl isocyanates, typically in the presence of a suitable base.

For the conversion of at least one hydroxy or amino group as substituent in a compound of formula I into lower alkoxy, carbamoylmethoxy, carboxymethoxy, benzyloxycarbonylmethoxy, lower alkoxycarbonylmethoxy or lower alkylamino, alkylation, preferably in the presence of a suitable base, is suitable. A suitable alkylating agent is, for example, a corresponding alkyl halide which is used at preferred temperatures of from 10 to 140° C., especially at about room temperature.

Those and other conversions can be found also in International Application WO 95/23141, published on Aug. 31, 1995, which is incorporated herein by reference.

Salts of compounds of formula I having a salt-forming group can be prepared in a manner known per se. For example, acid addition salts of compounds of formula I can be obtained, for example, by treatment with an acid or a suitable anion exchange reagent.

Salts can be converted into the free compounds in customary manner, for example by treatment with a suitable basic agent.

By treatment of free compounds of formula I obtained in that manner with acid addition salts it is possible to convert salts of compounds of formula I into other salts.

Stereoisomeric mixtures, for example mixtures of diastereoisomers, cis/trans isomers or enantiomers, can be separated into the corresponding isomers in a manner known perse by suitable separating procedures. For example, mixtures of diastereoisomers can be separated into the individual diastereoisomers by fractional crystallization, chromatography, solvent partition and the like. Such a separation can be carried out either at the stage of one of the starting materials or with the compounds of formula I themselves.

Starting Materials

The starting materials of formula II are novel, are known or can be prepared according to procedures known per se. They can be prepared in accordance with procedures analogous to those described in German Offenlegungsschriften No. 28 18 676 (published on Nov. 8th 1979) and No. 30 36 390 (published on May 13th 1982) and European Patent Application EP 0 682 027 (published on Nov. 15th 1995).

The starting material of formula II wherein X is chlorine is obtained, for example, from a compound analogous to formula II wherein X is hydroxy by reaction with phosphorus oxychloride (phosphoryl chloride, $P(=O)Cl_3$), with the exclusion of moisture, at reflux temperature. If desired, the further reaction of the resulting starting material of formula II wherein X is chlorine with an aza compound of formula III can be carried out in the same vessel, that is to say as a one-pot process. For that purpose the reaction mixture from the reaction with phosphorus oxychloride is concentrated to dryness by evaporation when the reaction is complete, made into a slurry with a suitable solvent, such as n-butanol, and reacted further with the aza compound of formula III.

A compound analogous to formula II wherein X is hydroxy (i.e. an isomer of a compound of formula IV) is obtained, for example, from a compound of formula V

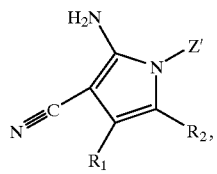

(V)

wherein Z' is 1-aryl-lower alkyl and the other substituents are as defined above, by reaction with formic acid, which is preferably used in excess with respect to the compound of formula V, for example in from 10- to 30-fold molar excess, optionally in the presence of an inert solvent, such as dimethylformamide, at elevated temperature, for example at temperatures of from 80° C. to the boiling temperature.

Alternatively, a compound analogous to formula II wherein X is hydroxy and the other symbols are as defined above is obtained, for example, from a compound of formula VI

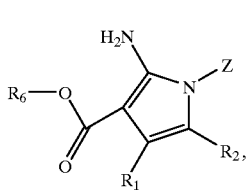

(VI)

wherein $R_6$ is lower alkyl, such as especially ethyl, and the other substituents are as defined above, by reaction with a large excess of formamide in a mixture of anhydrous dimethylformamide and formic acid. The reaction is carried out at elevated temperature, for example from 100° C. to 150° C., and preferably under a protective gas.

The 1-(Z')-2-amino-3-cyano-pyrroles of formula V used as intermediates can be prepared in good yields in accordance with published procedures known per se [see, for example, Roth, H. J., and Eger, K., Arch. Pharmaz. 308, 179 (1975)]. For that purpose, for example, a compound of formula VII

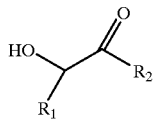

(VII)

is reacted first with an amine of formula Z'—NH$_2$ to form a compound of formula VIII

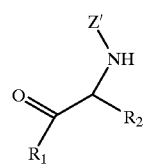

(VIII)

which is then converted with malonic acid dinitrile of the formula CH$_2$(CN)$_2$ into the desired intermediate of formula V. In detail, the reaction with the amine Z'—NH$_2$ is carried out under customary condensation conditions, for example in the presence of catalytic amounts of a strong acid, for example hydrochloric acid or p-toluenesulfonic acid, at elevated temperature (preferably boiling temperature) in a suitable solvent, for example benzene or toluene, with the separation of water, to form the respective a-aminoketone of formula VIII. The latter is not isolated but is immediately condensed with malonic acid dinitrile while hot, with the separation of water being continued, if necessary with the addition of a small amount of a base, such as piperidine, yielding a compound of formula V.

The compounds of formula VI used as intermediates wherein $R_2$ is N-benzyl-pyridonium-2-yl and the other substituents are as defined above are obtained, for example, by reaction of a compound of formula VI wherein $R_2$ is hydrogen and the other substituents are as defined above with N-benzyl-2-bromopyridonium bromide in a suitable solvent, such as a halogenated hydrocarbon, such as especially methylene chloride. The reaction is preferably carried out under a protective gas, in the dark and under anhydrous conditions at room temperature or elevated temperature, for example from 20° C. to 80° C., and in the presence of 2,6-dimethylpyridine (2,6-lutidine). The other compounds of formula VI are obtained, for example, by reaction of a 2-amidino-acetic acid lower alkyl ester of formula IX

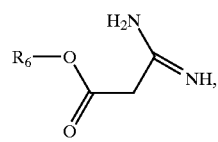

(IX)

wherein $R_6$ is as defined above, with a 2-X-1-$R_2$-ethan-1-one derivative of formula X

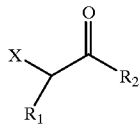

(X)

wherein the substituents are as defined above. The leaving group X is preferably bromine. Before the reaction begins, the 2-amidino-acetic acid lower alkyl ester of formula IX is liberated from its acid addition salt, such as especially its hydrochloride, with the aid of equimolar amounts of a base, such as especially sodium ethanolate, with ice-cooling. The reaction is carried out in a suitable solvent, especially a lower alkanol, such as preferably ethanol, at preferred temperatures of from 0° C. to 50° C., especially at room temperature.

Aza compounds of formula III are known or can be prepared according to methods known per se; some of them are also commercially available.

For example, an aza compound of formula III can be prepared in accordance with one of the procedures described in International Application WO 95/23141, published on Aug. 31st 1995, which is incorporated herein by reference, or in accordance with the references given therein.

For example, 2,3-dihydro-1,4-benzoxazine derivatives can be prepared according to R. C. Elderfield et al., Chapter 12 in "Heterocyclic Compounds", Vol. 6, R. C. Elderfield Ed., John Wiley & Sons, Inc., New York 1957; substituted 2,3-dihydrobenzothiazinyl compounds analogously to R. C. Elderfield et al., Chapter 13 of the same book; 1,2,3,4- tetrahydroquinolines and their starting materials analogously to "The Chemistry of Heterocyclic Compounds", Vol. 32, Parts 1, 2 and 3; G. Jones (Ed.), John Wiley and Sons, New York 1977; 1,2,3,4-tetrahydroquinolines substituted by lower alkyl or by unsubstituted or substituted phenyl by catalytic reduction of the corresponding quinolines using platinum oxide/hydrogen in methanol (see Honel et al., J. Chem. Soc. Perkin I 1980, 1933–1939); substituted 2,3,4,5-tetrahydro-1H-benzo[b]azepines analogously to G. R. Proctor, Chapter II, Vol 43, "The Chemistry of Heterocyclic Compounds", Part I; A. Rosowsky (Ed.), Wiley Interscience, New York 1984; and certain 2,3,4,5-tetrahydro-1H-benzo[b]azepines and 1,2,3,4,5,6-hexahydro-1H-benzo[b]azocines by reduction from the corresponding 2,3,4,5-tetrahydro-1H-benzo[b]azepin-2-ones and 1,2,3,4,5,6-hexahydro-1H-benzo[b]azocin-2-ones (see Horning et al., J. Am. Chem. Soc. 74, 5153 (1952) and Huisgen et al., Liebigs Ann. Chem. 586, 30 (1954)).

Aza compounds of formula III of the indoline type can be prepared by a series of reactions known per se.

For example, it is possible to obtain the indoline compounds of formula III especially by reduction of corresponding indole starting compounds. For that purpose, generally the corresponding indole precursors, in which the substituents ($R_3$ and/or $R_4$) are aprotic or appropriately protected, are reacted with $ZnBH_4$ (prepared from $ZnCl_2$, see Gensler et at, J. Am. Chem. Soc. 82, 6074–6081 (1960)) in an ethereal solvent, such as diethyl ether, at a temperature of from approximately 10 to approximately 40° C., preferably at room temperature (see Korsuki etal, Heterocycles 26, 1771–1774 (1987)); or the indole starting compound is reacted with a borane/pyridine complex (or another borane/tert-amine complex) in the presence or absence of a solvent, such as tetrahydrofuran, at a temperature of approximately from 10 to 30° C., preferably at room temperature, and then subjected to treatment with an acid, such as hydrochloric acid, trifluoroacetic acid or acetic acid, to form the indoline compound.

Some indoline compounds of formula III can be prepared from other indoline compounds by further modification. For example, unsubstituted or suitably substituted 5-hydroxyindolines can be prepared from the corresponding indolines by hydroxylation (see Teuber et at, Chem. Ber. 89, 489–508 (1956)) and subsequent reduction of the intermediate 5-hydroxyindoles to form the 5-hydroxyindolines: potassium nitrosodisulfonate in aqueous phosphate buffer is added to the unsubstituted or appropriately substituted indoline in acetone at neutral pH and a temperature of approximately from 0 to 25° C.; the resulting 5-hydroxyindole derivative is then reacted with borane/pyridine/aqueous HCl to form the 5-hydroxyindoline derivative. Unsubstituted or suitably substituted bromoindolines (for example brominated in the 4- or 6-position) can be obtained from corresponding indolines via bromination (see Miyake et al., J. Het. Chem. 20, 349–352 (1983)). That procedure can also be used for the bromination of larger ring systems (for example 1,2,3,4-tetrahydro-quinolines, 2,3,4,5-tetrahydro-1H-benzo[b]azepines and 1,2,3,4,5,6-hexahydro-benzo[b]-azocines, especially in the 5/7-, 6/8- and 7/9-positions). For that purpose, generally the unsubstituted or suitably substituted indoline is reacted with bromine in the presence of a halophile, such as silver sulfate, under strongly acidic conditions and at from 0 to 25° C. In addition, certain indolines with or without 3-alkyl substituents can be prepared from the corresponding 2-(2-halophenyl)alkylamines (see German Patent Application DE 34 24 900). Furthermore, hydroxyalkylindolines can be prepared by reduction of corresponding carboxy precursors or of esters thereof (see Corey et al., J. Am. Chem. Soc. 92(8), 2476–2488 (1970)). Suitably substituted lower alkyl-, lower alkenyl- or allyl-substituted indolines can be prepared from corresponding trialkylsilyl-protected 4-, 5- or 6-haloindoles by nickelphosphinecatalyzed Grignard addition (see Tamao et al., Bull. Chem. Soc. Japan 49, 1958–1969 (1976)), in which case the indoline is generally N-protected by reaction with tert-butyldimethyl-silyl triflate in a halogenated solvent in the presence of a tertiary amine. The N-silylated haloindoline is then reacted with the corresponding alkyl-, alkenyl- or allyl-Grignard in an ethereal solvent in the presence of a suitable nickel-phosphine complex (typically bis-(triphenylphosphine)nickel(II) dichloride). Subsequent treatment with methanol that contains a trace of an acid, such as trifluoroacetic acid, or with fluoride anions in a suitable solvent, such as tetrahydrofuran, frees the desired indoline derivative.

In addition, a 4-, 5-, 6- or 7-lower alkenyi-indoline or a free or tri-lower alkylsilyl-substituted lower alkynyl-indoline can be obtained by palladium-catalyzed vinylation or alkynylation of a corresponding 4-, 5-, 6- or 7-haloindoline (see Kalinin, Synthesis 1992, 413–432). For the preparation of the lower alkynylindoline, the corresponding bromo- or iodo-indoline is reacted under reflux with a suitable lower alkyne or with trimethylsilylacetylene or an analogue thereof in the presence of a catalytic amount of CuI and $Pd(PPh_3)$.

3,3-Dimethylindoline can be prepared, for example, by Lewis-acid-mediated cyclization of N-methylallylacetanilide, followed by hydrolysis (see Synthetic Communications 25(24), 4029–4033). A suitable Lewis acid is, for example, $AlCl_3$; the hydrolysis is carried out, for example, in the presence of hydrogen chloride.

Further preparation methods for numerous indolines, indoles, oxindoles and isatins that can be used as intermediates can be found in the literature (see "Heterocyclic Compounds with Indole and Carbazole Systems", W. C. Sumpter and F. Miller, in "The Chemistry of Heterocyclic Compounds", Vol. 8, Interscience Publishers Inc., New York 1954, and the references given therein).

The other starting compounds are known, can be prepared according to procedures known per se or are commercially available.

The reaction conditions used for the preparation of the starting materials are especially analogous to the reaction conditions to be found in the description and especially in the Examples.

General Process Conditions

All the process steps given in this text can be carried out under reaction conditions known perse, but preferably under those specifically mentioned, in the absence or usually in the presence of solvents or diluents, preferably those solvents or diluents that are inert towards the reagents used and are solvents there for, in the absence or presence of catalysts, condensation agents or neutralizing agents, for example ion exchangers, such as cation exchangers, for example in the $H^+$ form, depending upon the nature of the reaction and/or the reactants at reduced, normal or elevated temperature, for example in a temperature range of from approximately −100° to approximately 190° C., preferably from approximately −80° to approximately 150° C., for example from −80° to −60° C., at room temperature, at from −20° to 40° C. or approximately at the boiling point of the solvent used, under atmospheric pressure or in a closed vessel, optionally under pressure, and/or in an inert atmosphere, for example under an argon or nitrogen atmosphere.

In the case of all starting materials and intermediates, salts may be present when salt-forming groups are present. Salts may also be present during the reaction of such compounds, provided that the reaction will not be affected.

In all reaction steps, any isomeric mixtures that are formed can be separated into the individual isomers, for example diastereoisomers or enantiomers, or into any desired mixtures of isomers, for example racemates or diastereoisomeric mixtures, for example analogously to the methods described under the heading "Additional process steps".

In certain cases, for example in the case of hydrogenation, it is possible to carry out stereo-selective reactions so that, for example, individual isomers may be obtained more easily.

The solvents from which those suitable for a particular reaction can be selected include, for example, water, esters, such as lower alkyl lower alkanoates, for example ethyl acetate, ethers, such as aliphatic ethers, for example diethyl ether, or cyclic ethers, for example tetrahydrofuran, liquid aromatic hydrocarbons, such as benzene or toluene, alcohols, such as methanol, ethanol or 1- or 2-propanol, nitriles, such as acetonitrile, halogenated hydrocarbons, such as methylene chloride, acid amides, such as dimethylformamide, bases, such as heterocyclic nitrogen bases, for example pyridine, carboxylic acid anhydrides, such as lower alkanoic acid anhydrides, for example acetic anhydride, cyclic, linear or branched hydrocarbons, such as cyclohexane, hexane or isopentane, or mixtures of those solvents, for example aqueous solutions, unless the description of the processes indicates otherwise. Such solvent mixtures can also be used in working-up, for example by chromatography or partition.

The invention relates also to those forms of the process in which a compound obtainable as intermediate at any stage is used as starting material and the remaining steps are carried out or the process is interrupted at any stage or a starting material is formed under the reaction conditions or is used in the form of a reactive derivative or salt, or a compound obtainable in accordance with the process of the invention is produced under the process conditions and further processed in situ, it being preferable to use those starting materials which result in the compounds described above as being preferred, especially those described as being especially preferred, more especially preferred and/or very especially preferred.

The preparation of compounds of formula I (and also of intermediates) is preferably carried out analogously to the processes and process steps given in the Examples.

The compounds of formula I, including their salts, may also be obtained in the form of solvates, for example in the form of hydrates or, for example, in the form of crystals that include the solvent used for crystallization.

Pharmaceutical Compositions, the Preparation Thereof and the use According to the Invention of Compounds of Formula I and Compositions Comprising Those Compounds as Active Ingredient The present invention relates also to pharmaceutical compositions that comprise one of the compounds of formula I as active ingredient and that can be used especially in the treatment of the diseases mentioned at the beginning. Special preference is given to compositions for enteral, such as nasal, buccal, rectal or especially oral, administration and parenteral, such as intravenous, intramuscular or subcutaneous, administration to warm-blooded animals, especially human beings. The compositions comprise the active ingredient on its own or preferably together with a pharmaceutically acceptable carrier. The dose of the active ingredient depends on the disease to be treated, and on species, age, weight and individual condition, individual pharmacokinetic data, the disease to be treated and the mode of administration.

The invention relates also to pharmaceutical compositions for use in a method for the therapeutic treatment of the human or animal body, a process for the preparation thereof (especially as agents in tumor treatment) and a method of treating the above-mentioned diseases, especially a tumor disease, more especially one of those mentioned above, or psoriasis.

Preference is given to a pharmaceutical composition suitable for administration to a warm-blooded animal, especially a human being, suffering from a disease that is responsive to the inhibition of a protein kinase, especially psoriasis or a tumor disease, comprising a compound of formula I, or a salt thereof where salt-forming groups are present, in an amount effective in the inhibition of the protein kinase, together with at least one pharmaceutically acceptable carrier.

The pharmaceutical compositions comprise from approximately 1% to approximately 95% active ingredient, forms of administration in single dose form preferably comprising from approximately 20% to approximately 90% active ingredient and forms of administration that are not in single dose form preferably comprising from approximately 5% to approximately 20% active ingredient. Unit dose forms are, for example, dragees, tablets, ampoules, vials, suppositories or capsules. Other forms of administration are, for example, ointments, creams, pastes, foams, tinctures, lipsticks, drops, sprays, dispersions, etc. Examples are capsules comprising from approximately 0.05 g to approximately 1.0 g of the active ingredient.

The pharmaceutical compositions of the present invention are prepared in a manner known per se, for example by means of conventional mixing, granulating, confectioning, dissolving or lyophilizing procedures.

Solutions of the active ingredient, and also suspensions or dispersions, especially isotonic aqueous solutions, dispersion or suspensions, are preferably used, it being possible, for example in the case of lyophilized compositions that comprise the active ingredient alone or together with a carrier, for example mannitol, for such solutions, suspensions or dispersions to be made up prior to use. The pharmaceutical compositions may be sterilized and/or may comprise excipients, for example preservatives, stabilizers, wetting agents and/or emulsifiers, solubilizers, salts for regulating the osmotic pressure and/or buffers, and are prepared in a manner known per se, for example by means of conventional dissolving or lyophilizing procedures. The said solutions or suspensions may comprise viscosity-increasing substances, such as sodium carboxymethylcellulose, carboxymethylcellulose, dextran, polyvinylpyrrolidone or gelatin.

Suspensions in oil comprise as the oil component the vegetable, synthetic or semi-synthetic oils customary for injection purposes. There may be mentioned as such especially liquid fatty acid esters that contain as acid component a long-chained fatty acid having from 8 to 22, especially from 12 to 22, carbon atoms, for example lauric acid, tridecylic acid, myristic acid, pentadecylic acid, paimitic acid, margaric acid, stearic acid, arachidic acid, behenic acid, or corresponding unsaturated acids, for example oleic acid, elaidic acid, erucic acid, brassidic acid or linoleic acid, if desired with the addition of antioxidants, for example vitamin E, β-carotene or 3,5-di-tert-butyl-4-hydroxytoluene.

The alcohol component of those fatty acid esters has a maximum of 6 carbon atoms and is a mono- or poly-hydric, for example a mono-, di- or tri-hydric, alcohol, for example methanol, ethanol, propanol, butanol or pentanol or the isomers thereof, but especially glycol and glycerol. The following examples of fatty acid esters are therefore to be mentioned: ethyl oleate, isopropyl myristate, isopropyl palmitate, "Labrafil M 2375" (polyoxyethylene glycerol trioleate, Gattefossé, Paris), "Labrafil M 1944 CS" (unsaturated polyglycolized glycerides prepared by alcoholysis of apricot kernel oil and consisting of glycerides and polyethylene glycol ester; Gattefossé, France), "Labrasol" (saturated polyglycolized glycerides prepared by alcoholysis of TCM and consisting of glycerides and polyethylene glycol ester; Gattefossé, France) and/or "Miglyol 812" (triglyceride of saturated fatty acids with a chain length of $C_8$ to $C_{12}$, Hüls AG, Germany), but especially vegetable oils, such as cottonseed oil, almond oil, olive oil, castor oil, sesame oil, soybean oil and more especially groundnut oil.

The injection compositions are prepared in customary manner under sterile conditions; the same applies also to introducing the compositions into, for example, ampoules or vials and sealing the containers.

Pharmaceutical compositions for oral administration can be obtained, for example, by combining the active ingredient with one or more solid carriers, if desired granulating a resulting mixture, and processing the mixture or granules, if desired, and if necessary by the addition of additional excipients, to form tablets or dragée cores.

Suitable carriers are especially fillers, such as sugars, for example lactose, saccharose, mannitol or sorbitol, cellulose preparations and/or calcium phosphates, for example tricalcium phosphate or calcium hydrogen phosphate, and also binders, such as starches, for example corn, wheat, rice or potato starch, methylcellulose, hydroxypropylmethylcellulose, sodium carboxymethylcellulose and/or polyvinylpyrrolidone, and/or, if desired, disintegrators, such as the above-mentioned starches, also carboxymethyl starch, crosslinked polyvinylpyrrolidone, or alginic acid or a salt thereof, such as sodium alginate. Additional excipients are especially flow conditioners and lubricants, for example silicic acid, talc, stearic acid or salts thereof, such as magnesium or calcium stearate, and/or polyethylene glycol, or derivatives thereof.

Dragée cores can be provided with suitable, optionally enteric, coatings, there being used inter alia concentrated sugar solutions which may contain gum arabic, talc, polyvinylpyrrolidone, polyethylene glycol and/or titanium dioxide, or coating solutions in suitable organic solvents or solvent mixtures, or, for the production of enteric coatings, solutions of suitable cellulose preparations, such as acetylcellulose phthalate or hydroxypropylmethyl-cellulose phthalate. Colorings or pigments may be added to the tablets or dragée coatings, for example for identification purposes or to indicate different doses of active ingredient.

Orally administrable pharmaceutical compositions also include dry-filled capsules consisting of gelatin, and also soft, sealed capsules consisting of gelatin and a plasticizer, such as glycerol or sorbitol. The dry-filled capsules may contain the active ingredient in the form of granules, for example in admixture with fillers, such as corn starch, binders and/or glidants, such as talc or magnesium stearate, and optionally stabilizers. In soft capsules, the active ingredient is preferably dissolved or suspended in suitable liquid excipients, such as fatty oils, paraffin oil or liquid polyethylene glycols or fatty acid esters of ethylene or propylene gylycol, to which stabilizers and detergents, for example of the polyoxyethylene sorbitan fatty acid ester type, may also be added.

Other oral forms of administration are, for example, syrups prepared in customary manner which comprise the active ingredient, for example, in suspended form and in a concentration of about 5% to 20%, preferably about 10%, or in a similar concentration that provides a suitable single dose, for example, when administered in measures of 5 or 10 ml. Also suitable are, for example, powdered or liquid concentrates for the preparation of shakes, for example in milk. Such concentrates may also be packaged in single dose quantities.

Suitable rectally administrable pharmaceutical compositions are, for example, suppositories that consist of a combination of the active ingredient and a suppository base. Suitable suppository bases are, for example, natural or synthetic triglycerides, paraffin hydrocarbons, polyethylene glycols or higher alkanols.

For parenteral administration there are suitable especially aqueous solutions of an active ingredient in water-soluble form, for example in the form of a water-soluble salt, or aqueous injection suspensions that contain viscosity-increasing substances, for example sodium carboxymethylcellulose, sorbitol and/or dextran, and, if desired, stabilizers. The active ingredient, optionally together with excipients, can also be in the form of a lyophilisate and can be made into a solution prior to parenteral administration by the addition of suitable solvents.

Solutions such as are used, for example, for parenteral administration can also be used as infusion solutions.

Preferred preservatives are, for example, antioxidants, such as ascorbic acid, or microbicides, such as sorbic acid or benzoic acid.

Ointments are oil-in-water emulsions that contain up to 70%, but preferably from 20 to 50%, water or aqueous phase. Suitable as fatty phase are especially hydrocarbons, for example Vaseline®, paraffin oil or hard paraffins, which, for the purpose of improving the water-binding capacity, preferably contain suitable hydroxy compounds, such as fatty alcohols or esters thereof, for example cetyl alcohol or wool wax alcohols, such as wool wax. Emulsifiers are corresponding lipophilic substances, such as sorbitan fatty acid esters (Spans®), for example sorbitan oleate and/or sorbitan isostearate. Additives to the aqueous phase are, for example, humectants, such as polyalcohols, for example glycerol, propylene glycol, sorbitol and/or polyethylene glycol, or preservatives and perfumes.

Fatty ointments are anhydrous and contain as base material especially hydrocarbons, for example paraffin, Vaseline® or paraffin oil, also natural or partially synthetic fats, for example coconut fatty acid triglyceride, or preferably hardened oils, for example hydrogenated groundnut or castor oil, and also fatty acid partial esters of glycerol, for example glycerol mono- and/or di-stearate, and also, for example, the fatty alcohols, emulsifiers and/or additives that increase the water-absorption mentioned in connection with the ointments.

Creams are oil-in-water emulsions that contain more than 50% water. As oily base material there are used especially fatty alcohols, for example lauryl, cetyl or stearyl alcohol, fatty acids, for example palmitic or stearic acid, liquid to solid waxes, for example isopropyl myristate, wool wax or beeswax, and/or hydrocarbons, for example Vaseline® (petrolatum) or paraffin oil. Suitable as emulsifiers are surface-active substances having predominantly hydrophilic properties, such as corresponding non-ionic emulsifiers, for example fatty acid esters of polyalcohols or ethyleneoxy adducts thereof, such as polyglyceric acid fatty acid esters or polyethylene sorbitan fatty acid esters (Tweens®), also polyoxyethylene fatty alcohol ethers or fatty acid esters, or corresponding ionic emulsifiers, such as alkali metal salts of fatty alcohol sulfates, for example sodium lauryl sulfate, sodium cetyl sulfate or sodium stearyl sulfate, which are customarily used in the presence of fatty alcohols, for example cetyl alcohol or stearyl alcohol. Additives to the aqueous phase are inter alia agents that reduce the drying out of the creams, for example polyalcohols, such as glycerol, sorbitol, propylene glycol and/or polyethylene glycols, and also preservatives and perfumes.

Pastes are creams and ointments having secretion-absorbing powder constituents, such as metal oxides, for example titanium oxide or zinc oxide, and also talc and/or aluminum silicates, the purpose of which is to bind any moisture or secretions present.

Foams are administered from pressurized containers and are liquid oil-in-water emulsions in aerosol form, there being used as propellants halogenated hydrocarbons, such as chlorofluoro-lower alkanes, for example dichlorodifluoromethane and dichlorotetrafluoroethane, or preferably non-halogenated gaseous hydrocarbons, air, $N_2O$ or carbon dioxide. As oily phase there are used inter alia those used above in connection with ointments and creams, and likewise the additives mentioned therein.

Tinctures and solutions generally have an aqueous-ethanolic base to which there are added inter alia polyalcohols, for example glycerol, glycols and/or polyethylene glycol, as humectants to reduce evaporation, and fat-restoring substances, such as fatty acid esters with low molecular weight polyethylene glycols, i.e. lipophilic substances soluble in the aqueous mixture as a replacement for the fatty susbtances removed from the skin by the ethanol, and, if necessary, other excipients and additives.

The invention relates also to a procedure or a method for the treatment of the above-mentioned pathological conditions, especially a tumor disease or psoriasis, more especially such diseases which are responsive to the inhibition of protein kinases. The compounds of formula I can be administered, prophylactically or therapeutically, as such or in the form of pharmaceutical compositions, preferably in an amount effective against the said diseases, to a warm-blooded animal, for example a human being, requiring such treatment, the compounds being used especially in the form of pharmaceutical compositions. In such treatment an individual of about 70 kg body weight will be administered a daily dose of from approximately 0.1 g to approximately 5 g, preferably from approximately 0.5 g to approximately 2 g, of a compound of the present invention.

The following Examples serve to illustrate the invention but do not limit the scope thereof.

The short names and abbreviations used have the following meanings:

| Abbreviations | |
| --- | --- |
| abs. | absolute (anhydrous) |
| DMF | dimethylformamide |
| FAB-MS | Fast Atom Bombardment mass spectroscopy |
| m.p. | melting point |
| MS | mass spectroscopy |
| $R_f$ | ratio of the seepage propagation in relation to the eluant in TLC |
| RT | room temperature |
| sat. | saturated |
| THF | tetrahydrofuran |
| TLC | thin-layer chromatography |

Remarks:

Unless defined more specifically, "hexane" is a mixture of the hexane isomers.

EXAMPLE 1

4-(2,3-Dihydroindol-1-yl)-5,6-dimethyl-7H-pyrrolo[2,3-d]pyrimidine

Under an argon atmosphere, 0.2 g (1.1 mmol) of 4-chloro-5,6-dimethyl-7H-pyrrolo[2,3-d]-pyrimidine (see Liebigs Ann. Chem. 1986(9), 1485–1505; CAS-Reg. No. 82703-38-6) and 0.15 ml (1.32 mmol) of 2,3-dihydroindole (Fluka, Buchs, Switzerland) in 5 ml of abs. n-butanol are heated at reflux for 2 hours until the starting material is no longer present in TLC. The reaction mixture is concentrated by evaporation in vacuo at 50° C. The brown residue is dissolved in 30 ml of ethyl acetate, and 10 ml of 1 N NaOH solution are added. The organic phase is separated off and washed three times with a small amount of water, dried and concentrated by evaporation. The crude product is dissolved in 10 ml of THF, and n-hexane is added until crystallization begins. Stirring is carried out at 0° C. and the product is filtered off with suction and dried under a high vacuum. Pure 4-(2,3-dihydroindol-1-yl)-5,6-dimethyl-7H-pyrrolo[2,3-d]pyrimidine is obtained in the form of colorless crystals having a melting point of 220–221° C. FAB-MS: $(M+H)^+$= 265 (corresponds to $C_{16}H_{16}N_4$); $R_f$ value (toluene-acetone—4:6)=0.46.

EXAMPLE 2

4-(6-Chloro-2.3-dihydroindol-1-yl)-5,6-dimethyl-7H-pyrrolo[2,3-d]pyrimidine

This product is prepared in a manner analogous to that described in Example 1 from 4-chloro-5,6-dimethyl-7H-pyrrolo[2,3-d]pyrimidine and 6-chloro-2,3-dihydroindole (1.1 equi-valents, see J. Org. Chem. 55(2), 580–584 (1990); CAS Reg. No. 52 537-00-5).

EXAMPLE 3

4-(6-Bromo-2,3-dihydroindol-1-yl)-5,6-dimethyl-7H-pyrrolo[2,3-d]pyrimidine

This product is prepared in a manner analogous to that described in Example 1 from 4-chioro-5,6-dimethyl-7H-pyrrolo[2,3-d]pyrimidine and 6-bromo-2,3-dihydroindole (1.1 equivalents, see WO 95/23141; CAS Reg. No. 63 839-24-7).

EXAMPLE 4

4-(6-Methyl-2,3-dihydroindol-1-yl)-5,6-dimethyl-7H1-pyrrolo[2,3-d]pyrimidine

This product is prepared in a manner analogous to that described in Example 1 from 4-chloro-5,6-dimethyl-7H-pyrrolo[2,3-d]pyrimidine and 6-methyl-2,3-dihydroindole (1.1 equivalents, see WO 95/23141; CAS Reg. No. 86 911-82-2).

EXAMPLE 5

4-(1,2,3,4-Tetrahydroquinolin-1-yl)-5,6-dimethyl-7H-pyrrolo[2,3-d]pyrimidine

This product is prepared in a manner analogous to that described in Example 1 from 4-chloro-5,6-dimethyl-7H-pyrrolo[2,3-d]pyrimidine and 1,2,3,4-tetrahydroquinoline (4 equivalents, Fluka, Buchs, Switzerland). M.p: 263–264° C.; FAB-MS: (M+H)$^+$=279 (corresponds to C$_{17}$H$_{18}$N$_4$); R$_f$ value (toluene-acetone—(4:6))=0.29.

EXAMPLE 6

4-(2,3-Dihydroindol-1-yl)-6-(4-nitro-phenyl)-7H-pyrrolo[2.3-d]pyrimidine

Under a nitrogen atmosphere, 0.5 g (1.82 mmol) of 4-chloro-6-(4-nitro-phenyl)-7H-pyrrolo-[2,3-d]pyrimidine and 0.43 ml (2.1 equivalents) of 2,3-dihydroindole in 10 ml of abs. n-butanol are heated at reflux for 1.5 hours until the starting material is no longer present in TLC, the desired product precipitating out and being filtered off. The brown crude product is stirred thoroughly in about 20 ml of 1N NaOH for about 15 minutes, and the suspension is filtered with suction and the residue is washed with water, n-butanol and hexane and dried under a high vacuum. 4-(2,3-Dihydroindol-1-yl)-6-(4-nitro-phenyl)-7H-pyrrolo[2,3-d]pyrimidine is obtained in the form of a rust-brown powder having a melting point of>300° C. FAB-MS: (M+H)$^+$=358 (corresponds to C$_{20}$H$_{15}$N$_5$O$_2$); R$_f$ value (toluene-acetone—4:6)=0.40.

The starting material is prepared as follows:

Step 6.1: 2-Amino-3-ethoxycarbonyl-5-(4-nitro-phenyl)-pyrrole

In a dry three-necked flask, under argon, 75 ml of abs. ethanol and 6.5 g (390 mmol) of 2-amidino-acetic acid ethyl ester hydrochloride [preparation see: *Liebigs Ann. Chem.*, 1895 (1977)] are cooled to 0–5° C. and 2.65 g (390 mmol) of sodium ethanolate are added. 5 g (195 mmol) of 2-bromo-1-(4-nitro-phenyl)-ethan-1-one are then added and the mixture is allowed to rise to room temperature and is stirred for a further 48 hours. The reaction mixture is then partitioned between water and ethyl acetate. The ethyl acetate phase is washed three times with water and once with sat. NaCl solution, dried and filtered, and the filtrate is concentrated by evaporation. The reddish-brown residue is made into a slurry in hexane, the title compound precipitating in the form of a crude product (purity 93%) which is used for the next step without further purification; MS: (M)$^+$=275.

Step 6.2: 4-Hydroxy-6-(4-nitro-phenyl)-7H-pyrrolo[2,3-d]pyrimidine 2.5 g (97 mmol) of 2-amino-3-ethoxycarbonyl-5-(4-nitro-phenyl)-pyrrole, 19.4 ml of formamide, 9.7 ml of DMF and 3.1 ml of formic acid are stirred together at 150° C. for 22 hours. 1 ml of isopropanol is added to the warm reaction mixture. After the reaction mixture has cooled, the precipitated product is filtered off and washed in succession 3 times with 10 ml of ethanol each time, twice with 10 ml of isopropanol each time and twice with 10 ml of hexane each time. The title compound is obtained in the form of rust-brown crystals which are used for the next step; MS: (M)$^+$=256.

Step 6.3: 4-Chloro-6-(4-nitro-phenyl)-7H-pyrrolo[2,3-d]pyrimidine

4-Chloro-6-(4-nitro-phenyl)-7H-pyrrolo[2,3-d]pyrimidine is prepared, with the exclusion of moisture, by heating 4-hydroxy-6-(4-nitro-phenyl)-7H-pyrrolo[2,3-d]pyrimidine to boiling point with an excess of POCl$_3$. The suspension is concentrated to a residual volume of 20 ml by evaporation. The residue is introduced in portions into water, neutralized with solid NaHCO$_3$, and 0.2 liter of ethyl acetate is added. Filtration and washing with hot THF yield the title compound, m.p. >280° C.; FAB-MS: (M+H)$^+$=275.

EXAMPLE 7

4-(2,3-Dihydroindol-1-yl)-6-(4-amino-phenyl)-7H-pyrrolo[2,3-d]pyrimidine 400 mg of 4-(2,3-dihydroindol-1-yl)-6-(4-nitro-phenyl)-7H-pyrrolo[2,3-d]pyrimidine (Example 6) are hydrogenated with 150 mg of Raney nickel in methanol/THF (35:20) at RT and normal pressure for 10 hours. The catalyst is filtered off and the solution is concentrated by evaporation. The residue is dissolved in THF and the product is precipitated by the addition of hexane. 4-(2,3-Dihydroindol-1-yl)-6-(4-amino-phenyl)-7H-pyrrolo[2,3-d]pyrimidine is obtained in the form of a colorless powder. M.p. >300° C.; FAB-MS: (M+H)$^+$=328 (corresponds to C$_{20}$H$_{17}$N$_5$); R$_f$ value (toluene-acetone—4:6)=0.21.

EXAMPLE 8

4-(6-Chloro-2,3-dihydroindol-1-yl)-6-(4-nitro-phenyl)-7H-pyrrolo[2,3-d]-pyrimidine This product is prepared in a manner analogous to that described in Example 6 from 4-chloro-6-(4-nitro-phenyl)-7H-pyrrolo[2,3-d]pyrimidine and 6-chloro-2,3-dihydroindole (1.1 equivalents).

EXAMPLE 9

4-(6-Chloro-2,3-dihydroindol-1-yl)-6-(4-amino-phenyl)-7H-pyrrolo[2,3-d]-pyrimidine This product is obtained in a manner analogous to that described in Example 7 by hydrogenation of 4-(6-chloro-2,3-dihydroindol-1-yl)-6-(4-nitro-phenyl)-7H-pyrrolo[2,3-d]-pyrimidine (Example 8) with Raney nickel.

EXAMPLE 10

4-(1,2,3,4-Tetrahydroquinolin-1-yl)-6-(4-nitro-phenyl)-7H-pyrrolo[2,3-d]-pyrimidine This product is prepared in a manner analogous to that described in Example 6 from 4-chloro-6-(4-nitro-phenyl)-7H-pyrrolo[2,3-d]pyrimidine and 1,2,3,4-tetrahydroquinoline (2.1 equivalents). FAB-MS: (M+H)$^+$=372 (corresponds to C$_{21}$H$_{17}$N$_5$O$_2$); R$_f$ value (toluene-acetone—4:6)=0.36.

EXAMPLE 11

4-(1,2,3,4-Tetrahydroquinolin-1-yl)-6-(4amino-phenyl)-7H-pyrrolo[2.3-d]-pyrimidine This product is obtained in a manner analogous to that described in Example 7 by hydrogenation of 4-(1,2,3,4-tetrahydroquinolin-1-yl)-6-(4-nitro-phenyl)-7H-pyrrolo[2,3-d]-pyrimidine (Example 10) with Raney nickel. M.p. 243–245° C.; FAB-MS: (M+H)$^+$=342 (corresponds to C$_{21}$H$_{19}$N$_5$); R$_f$ value (toluene-acetone—4:6)=0.25.

EXAMPLE 12

4-(2,3-Dihydroindol-1-yl)-6-(4-methoxy-phenyl)-7H-pyrrolo[2,3-d]-pyrimidine

This product is prepared in a manner analogous to that described in Example 1 from 4-chloro-6-(4-methoxy-phenyl)-7H-pyrrolo[2,3-d]pyrimidine and 2,3-dihydroindole (1.1 equivalents). M.p. >300° C.; FAB-MS: (M+H)$^+$=343 (corresponds to C$_{21}$H$_{18}$N$_4$O).

EXAMPLE 13

Dry-filled Capsules 5000 capsules, each comprising as active ingredient 0.25 g of one of the compounds of formula I mentioned in the preceding Examples, are prepared as follows:

| Composition | |
|---|---|
| active ingredient | 1250 g |
| talcum | 180 g |
| wheat starch | 120 g |
| magnesium stearate | 80 g |
| lactose | 20 g |

Preparation method: The powdered substances listed above are pressed through a sieve of 0.6 mm mesh size 0.33 g portions of the mixture are introduced into gelatin capsules using a capsule-filling machine.

EXAMPLE 14
Soft Capsules 5000 soft gelatin capsules, each comprising as active ingredient 0.05 g of one of the compounds of formula I mentioned in the preceding Examples, are prepared as follows:

| Composition | |
|---|---|
| active ingredient | 250 g |
| Lauroglycol | 2 liters |

Preparation method: The powdered active ingredient is suspended in Lauroglycol® (propylene glycol laurate, Gattefossé S. A., Saint Priest, France) and ground to a particle size of about 1 to 3 μm in a wet pulverizer 0.419 g portions of the mixture are then introduced into soft gelatin capsules using a capsule-filling machine.

EXAMPLE 15
Soft Capsules 5000 soft gelatin capsules, each comprising as active ingredient 0.05 g of one of the compounds of formula I mentioned in the preceding Examples, are prepared as follows:

| Composition | |
|---|---|
| active ingredient | 250 g |
| PEG 400 | 1 liter |
| Tween 80 | 1 liter |

Preparation method: The powdered active ingredient is suspended in PEG 400 (polyethylene glycol of $M_r$ from about 380 to about 420, Fluka, Switzerland) and Tween® 80 (polyoxyethylene sorbitan monolaurate, Atlas Chem. Ind., Inc., USA, supplied by Fluka, Switzerland) and ground to a particle size of about 1 to 3 μm in a wet pulverizer. 0.43 g portions of the mixture are then introduced into soft gelatin capsules using a capsule-filling machine.

EXAMPLE 16
Inhibition of the EGF-receptor-specific Tyrosine Kinase

In accordance with the method mentioned above and using the recombinant intracellular domain of the EGF receptor (Europ. J. Biochem. 207, 265–275 (1992)), the following $IC_{50}$ values are obtained:

| Compound of Example | $IC_{50}$ (μM) |
|---|---|
| 1 | 1.56 |
| 5 | 2.69 |
| 7 | 0.21 |
| 11 | 0.026 |

EXAMPLE 17
Inhibition of the Growth of MK (mouse keratinocvte) Cells In Vitro:

The growth of BALB/MK cells in the presence of compounds of formula I is tested in accordance with the procedure described above. The following inhibition values ($IC_{50}$) are obtained:

| Compound of Example | $IC_{50}$ (μM) |
|---|---|
| 7 | 15.8 |
| 11 | 0.76 |

EXAMPLE 18
Inhibiton of the v-abl Kinase:

In accordance with the procedure mentioned above (Oncogene Research 5, 161–173 (1990) and Cancer Research 52, 4492–4498 (1992), the following $IC_{50}$ values are obtained:

| Compound of Example | $IC_{50}$ (μM) |
|---|---|
| 7 | 0.078 |
| 11 | 0.002 |

What is claimed is:

1. A compound of formula I

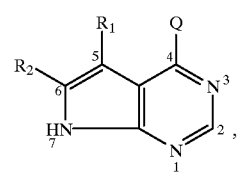

(I)

wherein $R_1$ and $R_2$ are each independently of the other lower alkyl; monohalo-, dihalo- or trihalo-lower alkyl; lower alkoxy; phenyl that is unsubstituted or substituted by halogen, monohalo-, dihalo- or trihalo-lower alkyl, carbamoyl-methoxy, carboxy-methoxy, benzyloxycarbonyl-methoxy, lower alkoxycarbonyl-methoxy, phenyl, amino, amino-lower alkyl, lower alkanoylamino, lower alkoxycarbonylamino, phenyl-lower alkoxycarbonylamino, furoyl, thienylcarbonyl, N-lower alkylamino, N,N-di-lower alkylamino, hydroxy, lower alkoxy, lower alkanoyloxy, carboxy, lower alkoxycarbonyl, carbamoyl, N-lower alkyl-carbamoyl, N,N-di-lower alkyl-carbamoyl, cyano, amidino, N-(N',N'-di-lower alkylaminomethylidene)-amino, N-((N', N'-di-lower alkylamino)-(lower alkyl)-methylidene)-amino, guanidino, ureido, $N^3$-lower alkylureido, $N^3,N^3$-di-lower alkylureido, thioureido, $N^3$-lower alkylthioureido, $N^3,N^3$-di-lower alkylthioureido, lower alkanesulfonylamino, benzeneor naphthalene-sulfonylamino that is unsubstituted or lower alkyl-substituted at the benzene or naphthalene ring, azido or by nitro; hydrogen; unsubstituted or halo- or lower alkyl-substituted pyridyl; N-benzyl-pyridonyl; naphthyl; cyano; carboxy; lower alkoxycarbonyl; carbamoyl; N-lower alkyl-carbamoyl; N,N-di-lower alkyl-carbamoyl; N-benzyl-carbamoyl; formyl; lower alkanoyl; lower alkenyl; lower alkenyloxy; or lower alkyl substituted by amino, lower alkylamino, piperazino, di-lower alkylamino, phenylamino or phenyl (each unsubstituted or substituted in the phenyl moiety by halogen, lower alkyl, hydroxy, lower alkanoyloxy, lower alkoxy, carboxy, lower alkoxycarbonyl, carbamoyl, N-lower alkylcarbamoyl, N,N-di-lower alkyl-carbamoyl, cyano, amidino, amino, amino-lower alkyl, lower alkanoylamino, lower alkylamino, N,N-di-lower alkylamino or by trifluoromethyl), hydroxy, lower alkoxy, cyano, carboxy, lower alkoxycarbonyl, carbamoyl, N-lower alkyl-carbamoyl, N,N-di-lower alkyl-carbamoyl, mercapto or by a radical of the formula $R_5$—$S(O_q)$— wherein $R_5$ is lower alkyl and q is 0, 1 or 2, and Q is a radical selected from the group consisting of 2,3-dihydroindol-1-yl,1,2,3,4-tetrahydroquinolin-1-yl, 2,3,4,5-tetrahydro-1H-benzo[b]azepin-1-yl, 1,2,3,4,5, 6-hexahydrobenzo[b]azocin-1-yl, 2,3,6,7,8,9-hexahydro-1H-benzo[g]indol-1-yl, 1,2,3,5-tetrahydropyrrolo[2,3-f]indol-1-yl and 1,2,3,5,6,7-hexahydro-pyrrolo[2,3-f]indol-1-yl; each of the mentioned radicals being unsubstituted or substituted by from 1 to 3 radicals selected independently of one another from the group consisting of lower alkyl, N,N-di-lower alkylamino-lower alkyl, lower alkynyl, tri-lower alkylsilanyl-lower alkynyl, halogen, nitro, hydroxy, lower alkoxy, isothiocyanato, unsubstituted phenyl, unsubstituted phenyl-lower alkoxy, carboxy, lower alkoxycarbonyl, amino, azido, lower alkanoylamino, trihalo-lower alkylcarbonylamino, pyrrol-1-yl and pyrrolidin-1-yl or substituted by lower alkylenedioxy that is formed by two radicals together and is bonded to two vicinal ring atoms;

or a salt thereof where at least one salt-forming group is present.

2. A compound of formula I according to claim 1, wherein $R_1$ and $R_2$ are each independently of the other selected from the group consisting of hydrogen; lower alkyl; and phenyl that is unsubstituted or substituted by halogen, monohalo-, dihalo- or trihalo-lower alkyl, carbamoyl-methoxy, carboxy-methoxy, benzyloxycarbonyl-methoxy, lower alkoxycarbonyl-methoxy, phenyl, amino, amino-lower alkyl, lower alkanoylamino, lower alkoxycarbonylamino, phenyl-lower alkoxycarbonylamino, furoyl, thienylcarbonyl, N-lower alkylamino, N,N-di-lower alkylamino, hydroxy, lower alkanoyloxy, carboxy, lower alkoxycarbonyl, carbamoyl, N-lower alkyl-carbamoyl, N,N-di-lower alkyl-carbamoyl, cyano, amidino, N-(N',N'-di-lower alkylaminomethylidene)-amino, N-((N',N'-di-lower alkylamino)-(lower alkyl)-methylidene)-amino, guanidino, ureido, $N^3$-lower alkylureido, $N^3,N^3$-di-lower alkylureido, thioureido, $N^3$-lower alkylthioureido, $N^3,N^3$-di-lower alkylthioureido, lower alkanesulfonylamino, benzene- or naphthalene-sulfonylamino that is unsubstituted or lower alkyl-substituted at the benzene or naphthalene ring, azido or by nitro, and Q is a radical selected from the group consisting of 2,3-dihydroindol-1-yl, 1,2,3,4-tetrahydroquinolin-1-yl, 2,3,4,5-tetrahydro-1H-benzo[b]azepin-1-yl, 1,2,3,4,5, 6-hexahydrobenzo[b]azocin-1-yl, 2,3,6,7,8,9-hexahydro-1H-benzo[g]indol-1-yl, 1,2,3,5-tetrahydropyrrolo[2,3-f]indol-1-yl and 1,2,3,5,6,7-hexahydro-pyrrolo[2,3-f]indol-1-yl; each of the mentioned radicals being unsubstituted or substituted by from 1 to 3 radicals selected independently of one another from the group consisting of lower alkyl, N,N-di-lower alkylamino-lower alkyl, lower alkynyl, tri-lower alkylsilanyl-lower alkynyl, halogen, nitro, hydroxy, lower alkoxy, isothiocyanato, unsubstituted phenyl, unsubstituted phenyl-lower alkoxy, carboxy, lower alkoxycarbonyl, amino, azido, lower alkanoylamino, trihalo-lower alkylcarbonylamino, pyrrol-1-yl and pyrrolidin-1-yl or substituted by lower alkylenedioxy that is formed by two radicals together and is bonded to two vicinal ring atoms;

or a salt thereof.

3. A compound of formula I according to claim 1 wherein either the two radicals $R_1$ and $R_2$ are each independently of the other lower alkyl;

or $R_1$ is hydrogen and $R_2$ is phenyl that is unsubstituted or substituted by amino, nitro or by methoxy; and Q is 2,3-dihydroindol-1-yl, 6-chloro-2,3-dihydroindol-1-yl, 6-bromo-2,3-dihydroindol-1-yl, 6-methyl-2,3-dihydroindol-1-yl or 1,2,3,4-tetrahydroquinolin-1-yl;

or a salt thereof.

4. A compound of formula I according to claim 1, selected from the group consisting of 4-(1,2,3,4-tetrahydroquinolin-1-yl)-5,6-dimethyl-7H-pyrrolo[2,3-d]pyrimidine, 4-(2,3-dihydroindol-1-yl)-6-(4-amino-phenyl)-7H-pyrrolo[2,3-d]pyrimidine, 4-(1,2,3,4-tetrahydroquinolin-1-yl)-6-(4-amino-phenyl)-7H-pyrrolo[2,3-d]pyrimidine and 4-(2,3-dihydroindol-1-yl)-6-(4-methoxy-phenyl)-7H-pyrrolo[2,3-d]pyrimidine, or a pharmaceutically acceptable salt thereof.

5. A compound of formula I according to claim 1, selected from the group consisting of 4-(6-chloro-2,3-dihydroindol-1-yl)-5,6-dimethyl-7H-pyrrolo[2,3-d]pyrimidine, 4-(6-bromo-2,3-dihydroindol-1-yl)-5,6-dimethyl-7H-pyrrolo[2,3-d]pyrimidine, 4-(6-methyl-2,3-dihydroindol-1-yl)-5,6-dimethyl-7H-pyrrolo[2,3-d]pyrimidine, 4-(2,3-dihydroindol-1-yl)-6-(4-nitro-phenyl)-7H-pyrrolo[2,3-d]pyrimidine, 4-(6-chloro-2,3-dihydroindol-1-yl)-6-(4-nitro-phenyl)-7H-pyrrolo[2,3-d]pyrimidine, 4-(6-chloro-2,3-dihydroindol-1-yl)-6-(4-amino-phenyl)-7H-pyrrolo[2,3-d]pyrimidine and 4-(1,2,3,4-tetrahydroquinolin-1-yl)-6-(4-nitro-phenyl)-7H-pyrrolo[2,3-d]pyrimidine, or a pharmaceutically acceptable salt thereof.

6. A process for the preparation of a 7H-pyrrolo[2,3-d]pyrimidine derivative of formula I according to claim 1 wherein a) a pyrrolo[2,3-d]pyrimidine derivative of formula II

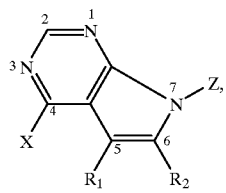

(II)

wherein X is a suitable leaving group, Z is hydrogen or 1-aryl-lower alkyl and the other substituents are as defined for compounds of formula I according to claim 1, free functional groups present in the radicals $R_1$ and $R_2$ being protected if necessary by readily removable protecting groups, is reacted with an aza compound of formula III

Q—H     (III), wherein Q is as defined for compounds of formula I according to claim 1, free functional groups present in the radical Q being protected if necessary by readily removable protecting groups, and any protecting groups and, if present, the 1-aryl-lower alkyl radical Z are removed, or b) a pyrrolo[2,3-d]pyrimidin-4-one derivative of formula IV

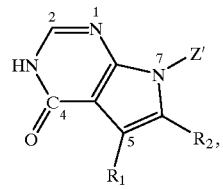

(IV)

wherein Z' is 1-aryl-lower alkyl and $R_1$ and $R_2$ are as defined for compounds of formula I according to claim 1 free functional groups present in the radicals $R_1$ and $R_2$ being protected if necessary by readily removable protecting groups, is reacted in the presence of a dehydrating agent and a tertiary amine with an aza compound of the above formula III and any protecting groups present are removed;

and, if desired, after carrying out one of the process variants a) and b), a compound of formula I is converted into a different compound of formula I; and/or, if necessary for the preparation of a salt, a resulting free compound of formula I is converted into a salt or, if necessary for the preparation of a free compound, a resulting salt of a compound of formula I is converted into the free compound; or an obtainable salt of a compound of formula I is converted into a different salt of a compound of formula 1.

7. A compound of formula I according to claim 1 in the form of a pharmaceutically acceptable salt.

8. A compound of formula I according to claim 2 in the form of a pharmaceutically acceptable salt.

9. A compound of formula I according to claim 5 in the form of a pharmaceutically acceptable salt.

10. The compound 4-(2,3-dihydroindol-1-yl)-5,6-dimethyl-7H-pyrrolo[2,3-d]pyrimidine according to claim 1, or a pharmaceutically acceptable salt thereof.

11. A pharmaceutical composition comprising of pharmaceutically acceptable carrier or diluent and a therapeutically effective amount of a compound according to claim 1, or a pharmaceutically acceptable salt thereof.

12. A method of treating tumors which are responsive to protein tyrosine kinase inhibition comprising administering to a warm-blooded animal in need of such treatment a therapeutically effective amount of a compound of claim 1, or a pharmaceutically acceptable salt thereof.

13. A method according to claim 12 wherein the warm-blooded animal is a human.

* * * * *